(12) United States Patent
Richlen et al.

(10) Patent No.: US 7,250,549 B2
(45) Date of Patent: Jul. 31, 2007

(54) THREE-PIECE GARMENT HAVING AN ABSORBENT INSERT SECURED WITH VARIABLE ADHESIVE REGIONS

(75) Inventors: Sandra A. Richlen, Black Creek, WI (US); Paul Christoffel, Appleton, WI (US); Suzanne M. Schmoker, Oshkosh, WI (US); Paul Hasler, Appleton, WI (US); Sarah Freiburger, Hortonville, WI (US); David F. Bishop, Appleton, WI (US); Melanie J. Milslagle, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 231 days.

(21) Appl. No.: 10/748,712

(22) Filed: Dec. 30, 2003

(65) Prior Publication Data

US 2005/0148965 A1 Jul. 7, 2005

(51) Int. Cl.
*A61F 13/15* (2006.01)
(52) U.S. Cl. .................. 604/367; 604/365; 604/358; 604/372; 604/373; 604/385.1; 156/238; 428/342; 428/343
(58) Field of Classification Search .............. 604/367, 604/358, 365, 372–373, 385.01; 156/238; 428/342–343
See application file for complete search history.

(56) References Cited

U.S. PATENT DOCUMENTS 4,055,182 A 10/1977 Mack (Continued)

FOREIGN PATENT DOCUMENTS

EP 0 661 033 A1 12/1993

(Continued)

OTHER PUBLICATIONS

International Search Report for PCT/US2004/030844, mailed Jan. 2005, 3 pages.

(Continued)

*Primary Examiner*—Tatyana Zalukaeva
*Assistant Examiner*—Ginger Chapman
(74) *Attorney, Agent, or Firm*—Brinks Hofer Gilson & Lione

(57) ABSTRACT

An absorbent garment includes a front body panel having a terminal waist edge and a terminal crotch edge and a rear body panel having a terminal waist edge and a terminal crotch edge. The terminal crotch edge of the rear body panel is longitudinally spaced from and forms a gap with the terminal crotch edge of the front body panel. An absorbent insert includes first and second longitudinally spaced end portions and opposite laterally spaced side edges. The absorbent insert bridges the gap between the front and rear body panels with the first and second end portions overlying and connected to the front and rear body panels respectively. At least one of the first and second end portions of the absorbent insert is connected respectively to a corresponding one of the front and rear body panels with at least first and second adhesive regions having first and second adhesive basis weights respectively. At least a portion of the second adhesive region is located adjacent the terminal crotch edge of at least one of the front and rear body panels. The second adhesive basis weight is greater than the first adhesive basis weight. In another aspect, the first adhesive region has a first peel strength and the first and second adhesive regions in combination have a second peel strength. In one embodiment, the second peel strength is greater than the first peel strength. In another aspect, a method of assembling the absorbent garment is provided.

19 Claims, 11 Drawing Sheets

U.S. PATENT DOCUMENTS

| | | | |
|---|---|---|---|
| 4,205,679 A * | 6/1980 | Repke et al. | 604/366 |
| 4,437,860 A | 3/1984 | Sigl et al. | |
| 4,521,490 A | 6/1985 | Pocius et al. | |
| 4,573,986 A | 3/1986 | Minetola et al. | |
| 4,578,073 A * | 3/1986 | Dysart et al. | 604/397 |
| 4,641,381 A | 2/1987 | Heran et al. | |
| 5,057,571 A | 10/1991 | Malcolm et al. | |
| 5,413,654 A | 5/1995 | Igaue et al. | |
| 5,622,581 A | 4/1997 | Ducker et al. | |
| 5,685,874 A | 11/1997 | Buell et al. | |
| 5,865,825 A | 2/1999 | Schlinz | |
| 5,874,157 A | 2/1999 | Robinson et al. | |
| 6,132,410 A * | 10/2000 | Van Gompel et al. | 604/385.25 |
| 6,217,563 B1 * | 4/2001 | Van Gompel et al. | 604/385.101 |
| 6,352,607 B1 | 3/2002 | Kuen et al. | |
| 6,369,291 B1 | 4/2002 | Uchimoto et al. | |
| 6,514,233 B1 | 2/2003 | Glaug | |
| 6,755,808 B2 * | 6/2004 | Balogh et al. | 604/385.28 |
| 7,066,921 B2 * | 6/2006 | Schmoker et al. | 604/385.01 |
| 7,163,740 B2 * | 1/2007 | Rosati et al. | 428/343 |
| 2003/0028166 A1 | 2/2003 | Price et al. | |
| 2003/0171728 A1 * | 9/2003 | Heyn et al. | 604/378 |
| 2004/0068246 A1 * | 4/2004 | Rose et al. | 604/385.27 |
| 2004/0122401 A1 * | 6/2004 | Van Gompel et al. | 604/385.14 |
| 2005/0137563 A1 * | 6/2005 | Van Gompel et al. | 604/385.27 |

FOREIGN PATENT DOCUMENTS

| | | | |
|---|---|---|---|
| EP | 0 368 141 B1 | | 6/1994 |
| EP | 0 923 921 A1 | | 6/1999 |
| EP | 1 013 251 A1 | | 6/2000 |
| EP | 1 230 864 A2 | | 8/2002 |
| EP | 1 249 214 A2 | | 10/2002 |
| EP | 1 366 735 A1 | | 12/2003 |
| WO | WO 98/16179 | | 4/1998 |
| WO | WO 99/32062 | | 4/1999 |
| WO | WO 99/32062 | * | 7/1999 |
| WO | WO 00/37005 | | 6/2000 |
| WO | WO 00/47151 | | 8/2000 |

OTHER PUBLICATIONS

Written Opinion of the International Searching Authority, PCT/US2004/030844, mailed Jan. 2005, 5 pages.

Drawing of RSR 4732 product used in testing prior to Dec. 30, 2002.

* cited by examiner

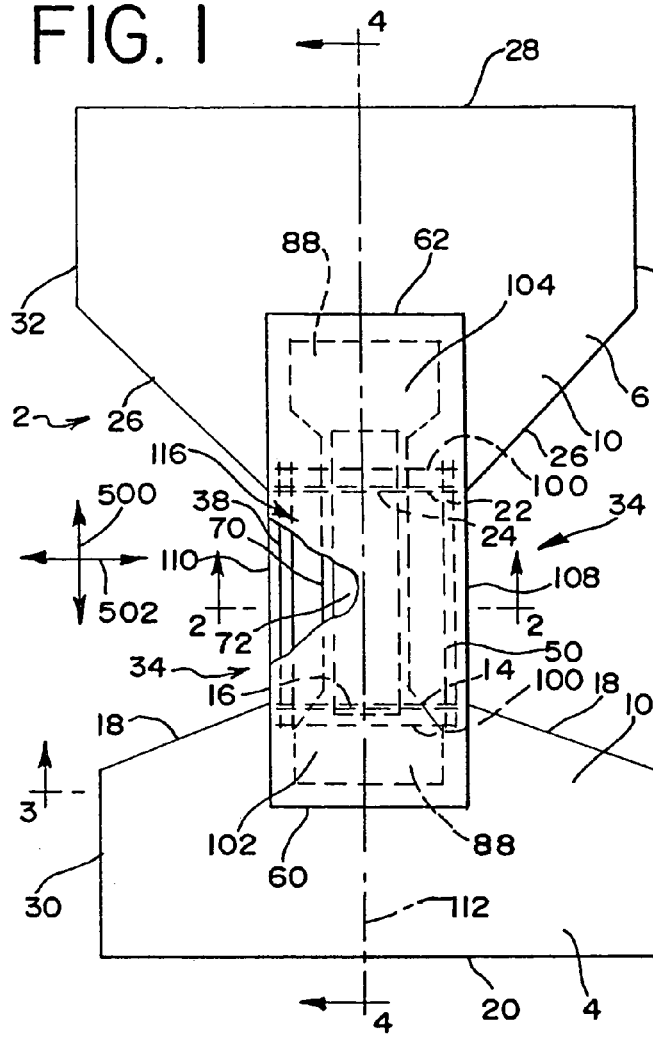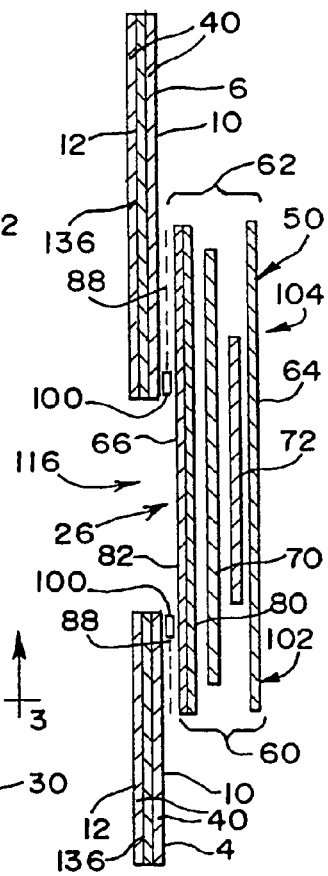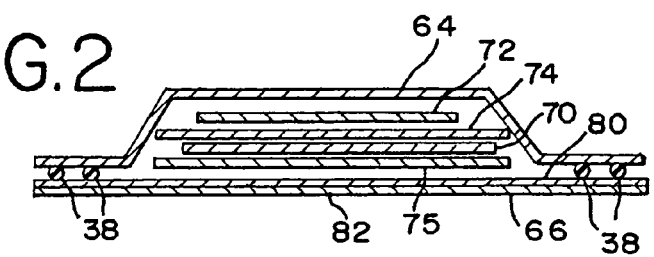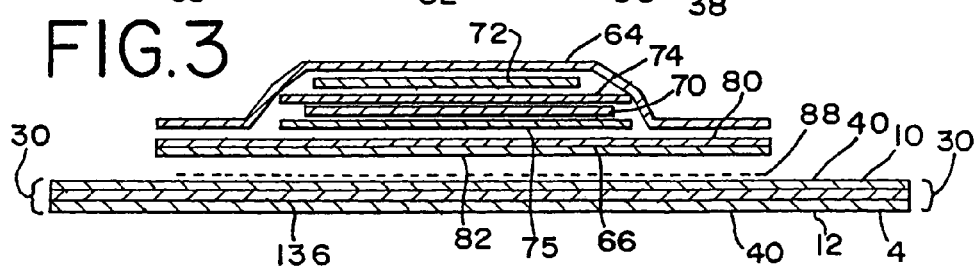

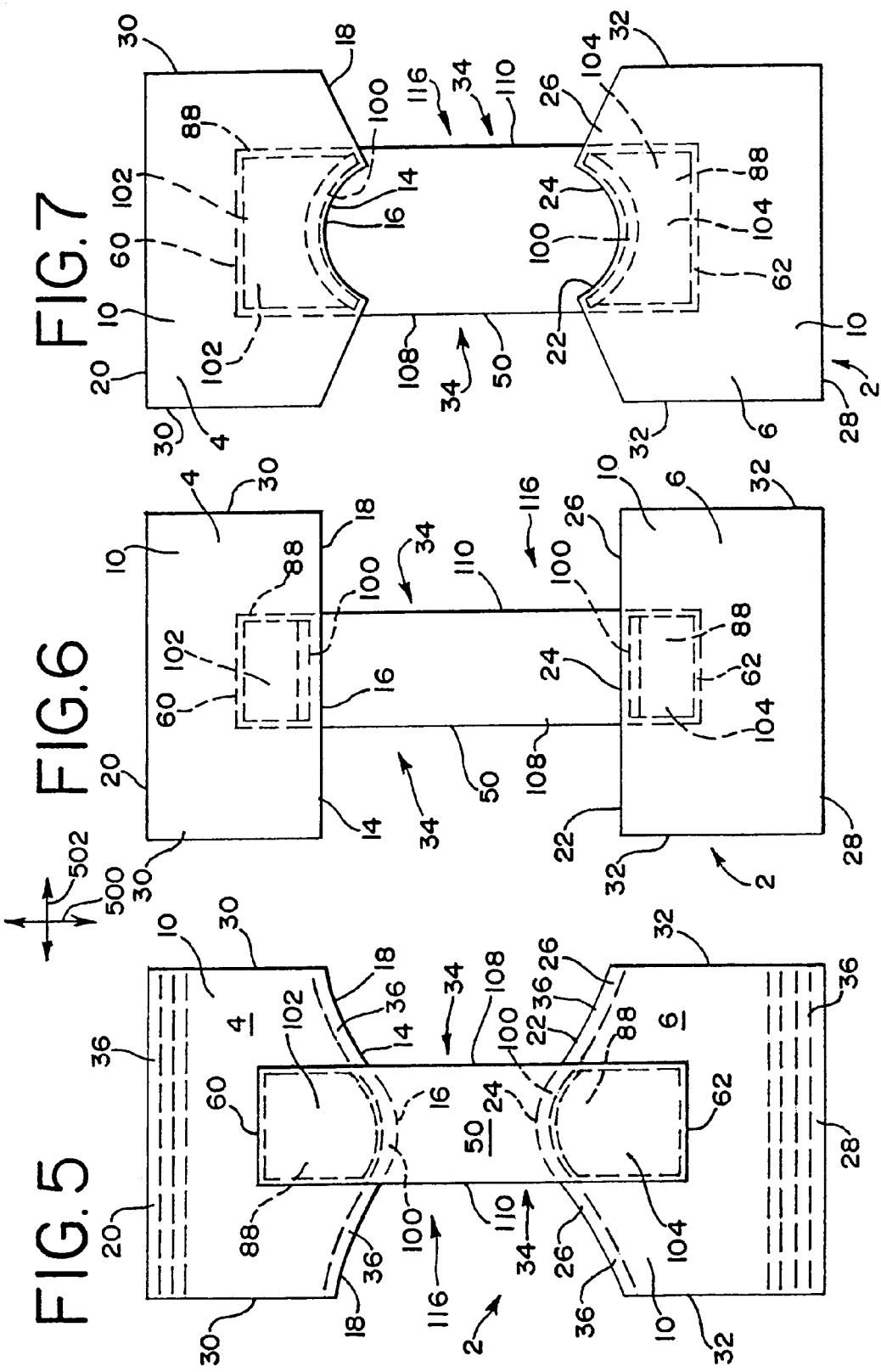

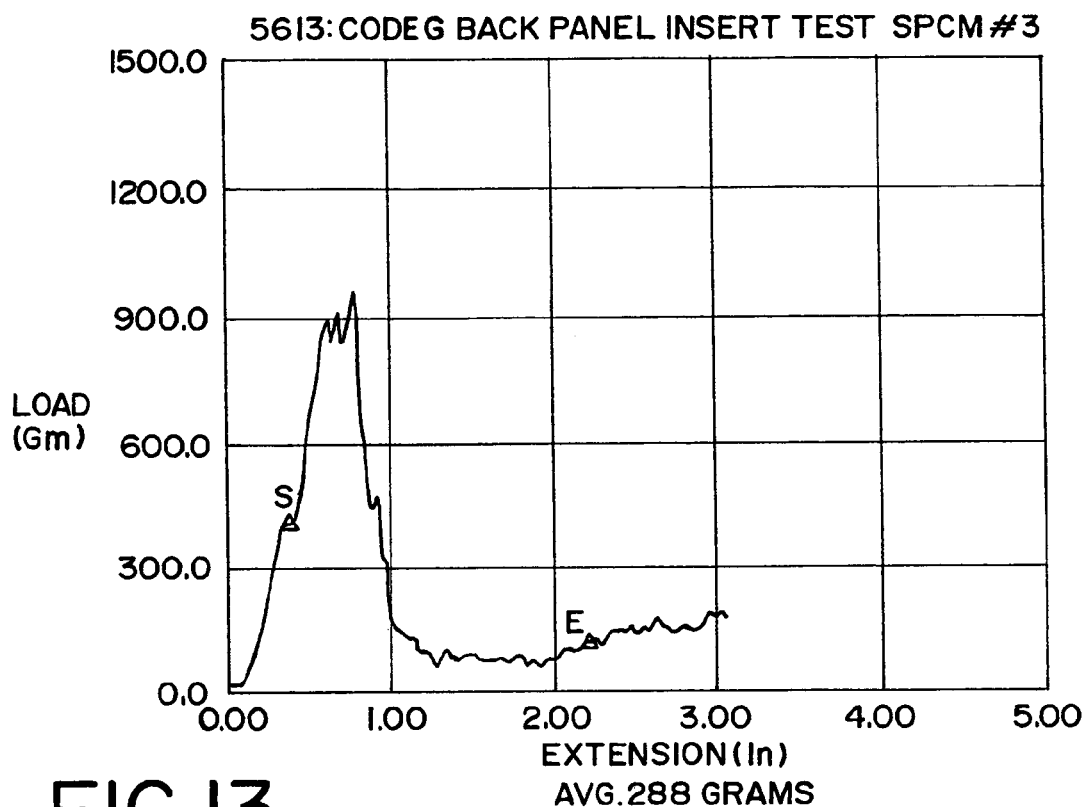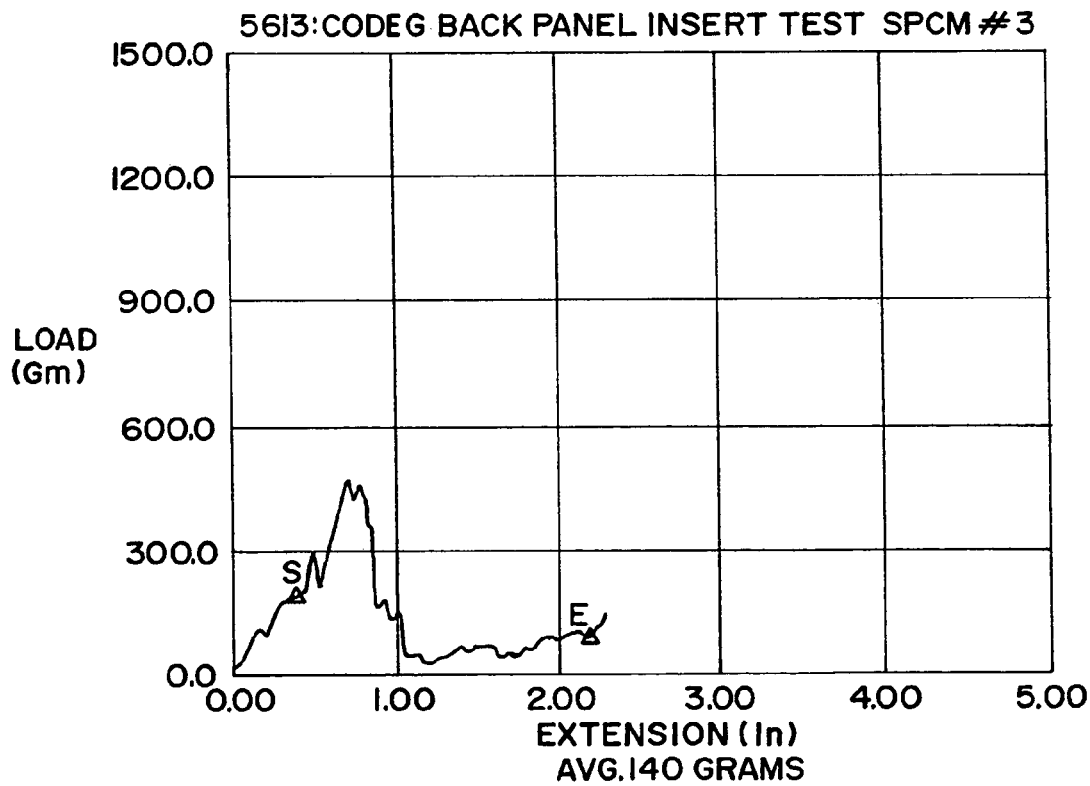

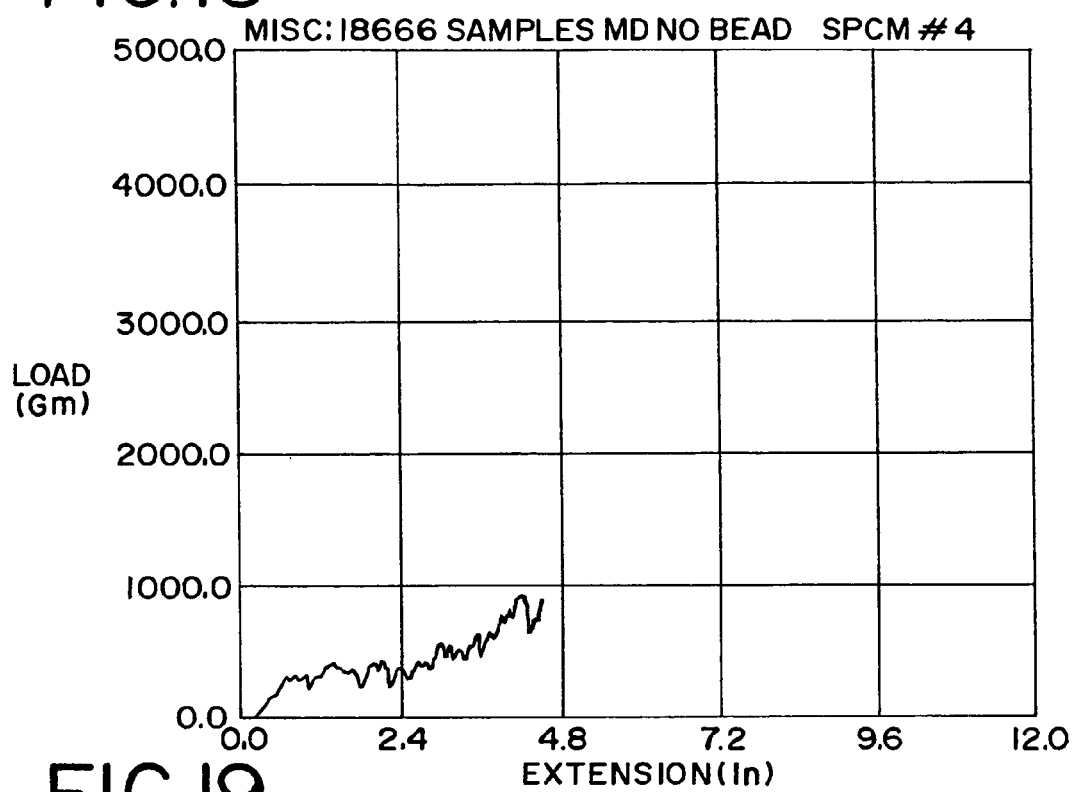
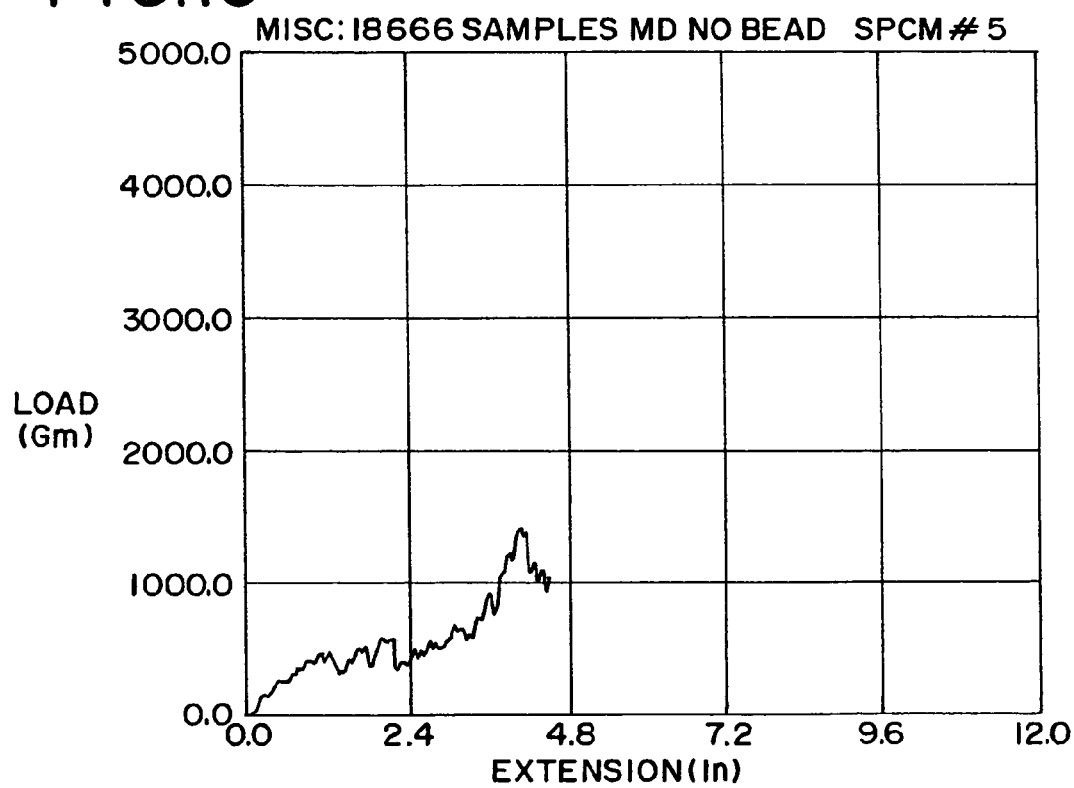

THREE-PIECE GARMENT HAVING AN ABSORBENT INSERT SECURED WITH VARIABLE ADHESIVE REGIONS

BACKGROUND

The present invention relates generally to undergarments, and in particular, to a three-piece garment having an absorbent insert secured to a body panel with variable adhesive regions.

Disposable garments can be configured in many different forms. For example, disposable absorbent garments can be configured as a pant-type, pull-on garment, or as a diaper-type product that is drawn up between the legs and fastened about the waist with various fastening systems. Typically, the absorbent garment includes an absorbent insert connected to one or more body panels. Typically, the absorbent insert is connected to the body panel(s) with an adhesive having a relatively uniform basis weight. Accordingly, the connection between the absorbent insert and the body panel(s) may be susceptible to separation in those areas where higher stresses are introduced as the garment is worn by the user.

SUMMARY

Briefly stated, in one aspect, an absorbent garment includes a front body panel having a terminal waist edge and a terminal crotch edge and a rear body panel having a terminal waist edge and a terminal crotch edge. The terminal crotch edge of the rear body panel is longitudinally spaced from and forms a gap with the terminal crotch edge of the front body panel. An absorbent insert includes first and second longitudinally spaced end portions and opposite laterally spaced side edges. The absorbent insert bridges the gap between the front and rear body panels with the first and second end portions overlying and connected to the front and rear body panels respectively. At least one of the first and second end portions of the absorbent insert is connected respectively to a corresponding one of the front and rear body panels with at least first and second adhesive regions having first and second adhesive basis weights respectively. At least a portion of the second adhesive region is located adjacent the terminal crotch edge of at least one of the front and rear body panels. The second adhesive basis weight is greater than the first adhesive basis weight.

In another aspect, the first adhesive region has a first peel strength, and the first and second adhesive regions in combination have a second peel strength. In one embodiment, the second peel strength is greater than the first peel strength.

In yet another aspect, a method of assembling an absorbent garment includes positioning the rear body panel relative to the front body panel such that the terminal crotch edge of the rear body panel is longitudinally spaced from and forms a gap with the terminal crotch edge of the front body panel, positioning the absorbent insert such that the absorbent insert bridges the gap between the front and rear body panels with the first and second end portions overlying the front and rear body panels respectively, and connecting at least one of the first and second end portions of the absorbent insert to a corresponding one of the front and rear body panels with at least first and second adhesive regions. The first and second adhesive regions can have, in various embodiments, first and second adhesive basis weights and first and second peel strengths.

The various aspects provide significant advantages over other disposable undergarments and methods. For example and without limitation, the second adhesive region enhances the integrity and performance of an undergarment having spaced apart front and rear body panels. In particular, the second adhesive region ensures that the absorbent insert does not become separated from one or both of the front and rear body panels adjacent the terminal crotch edges thereof, which area can experience increased stresses during use. The connection improves the overall product fit and performance and maintains a proper gasket with the user.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 1 is a plan view of one embodiment of an absorbent garment in an unfolded configuration with an absorbent insert connected to a bodyside surface of a front and rear body panel.

FIG. 2 is a cross sectional view of the absorbent garment shown in FIG. 1 taken along line 2—2.

FIG. 3 is a cross sectional view of the absorbent garment shown in FIG. 1 taken along line 3—3.

FIG. 4 is a cross-sectional view of the absorbent garment shown in FIG. 1 taken along line 4—4.

FIG. 5 is a plan view of another embodiment of an absorbent garment in an unfolded configuration with an absorbent insert connected to a bodyside surface of a front and rear body panel.

FIG. 6 is a plan view of another embodiment of an absorbent garment in an unfolded configuration with an absorbent insert connected to a garment side surface of a front and rear body panel.

FIG. 7 is a plan view of another embodiment of an absorbent garment in an unfolded configuration with an absorbent insert connected to a garment side surface of a front and rear body panel.

FIG. 12 is a load v. extension graph for a machine direction peel strength test.

FIG. 13 is a load v. extension graph for a machine direction peel strength test.

FIG. 18 is a load v. extension graph for a machine direction peel strength test.

FIG. 19 is a load v. extension graph for a machine direction peel strength test.

DETAILED DESCRIPTION OF THE PRESENTLY PREFERRED EMBODIMENTS

Figure 8:
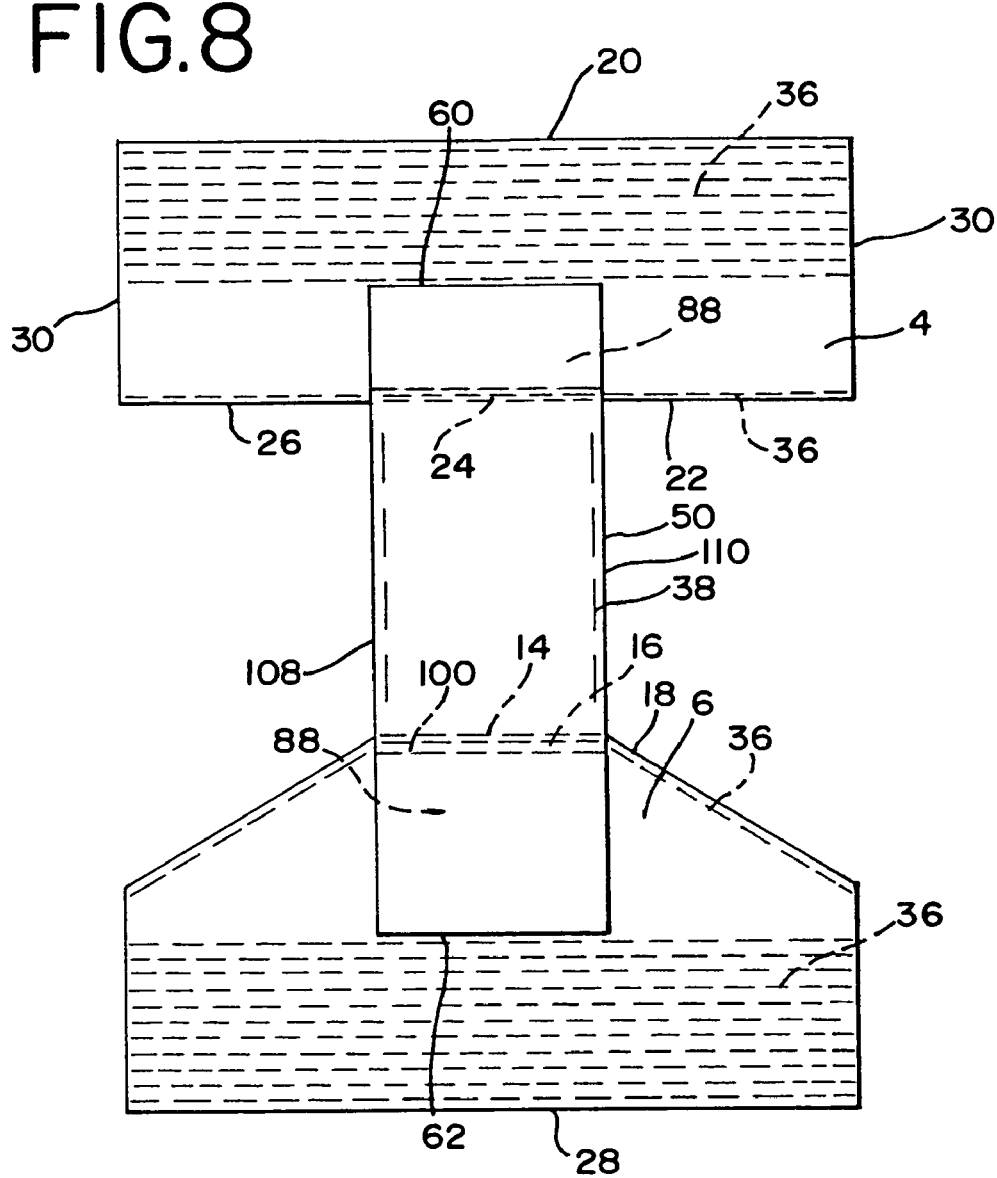
FIG. 8 is a plan view of another embodiment of an absorbent garment in an unfolded configuration.
Figure 9:
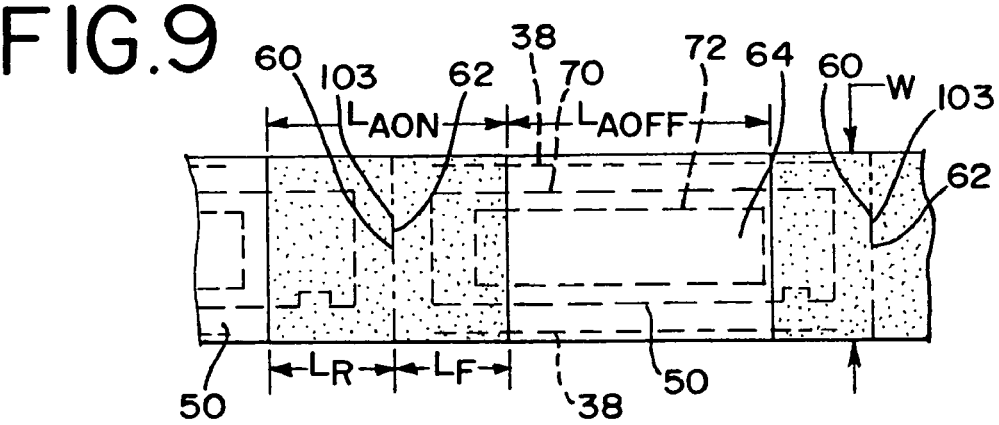
FIG. 9 is a plan view of an adhesive being applied to an absorbent insert web.

It should be understood that the term "longitudinal," as used herein, means of or relating to length or the lengthwise direction 500. The term "laterally," as used herein, means situated on, directed toward or running from side to side in a direction 502 substantially perpendicular to the lengthwise direction.

The term "bodyside" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The terms "connecting," "coupled," "attached," and "secured," and variations thereof, broadly covers two or more items being directly connected one to the other, or by way of one or more intervening members or components.

Referring to FIGS. 1 and 5–7, an undergarment 2 includes a first, front body panel 4 and a second, rear body panel 6. The term "body panel" refers to the portion(s) of the undergarment, whether made of one or more layers or substrates or of one or more pieces or components, that is/are fitted circumferentially around at least a portion of the waist region of the user, including for example the user's lower back, buttock, hips and abdomen. The first and second body panels each have an inner, bodyside surface 10 and an outer, garment side surface 12 (see FIG. 3). Referring to the embodiments of FIGS. 1, 5 and 6, the first, front body panel 4 has a first terminal crotch edge 14 forming a crotch portion 16 and leg opening portion 18 and a second terminal waist edge 20 which, in one embodiment, is linear but can assume other shapes. Likewise, the second, rear body panel 6 has a first terminal crotch edge 22 forming a crotch portion 24 and a leg opening portion 26 and a second terminal waist edge 28, which is shown linear but can assume other shapes. As shown in FIG. 6, the terminal crotch edges 14, 22 are substantially linear. Referring to FIG. 5, the terminal crotch edge is curvilinear, with the crotch portion 16 and leg opening portions 18 forming a generally sinusoidal curve, and with the crotch portion 16 having a convex contour. Referring to FIG. 7, the crotch portion 16 has a concave contour that provides access to an underlying absorbent insert 50. Of course, it should be understood that the crotch edge can have many forms and shapes not expressly disclosed herein. Each of the first and second body panels has an outboard side edge 30, 32 formed along the outer periphery of the opposite side portions of the first and second body panel. It should be understood that the outboard side edges of the front and rear body panels can have the same or different lengths relative to each other.

Referring to the exemplary embodiment shown in FIG. 5, one or more, and in one embodiment a plurality, meaning two or more, elastic elements 36 are secured to each of the first and second body panels. In preferred embodiment, a plurality of elastic elements are spaced across substantially the entire waist portion of the front and rear body panel 4, 6, although they may be spaced across a lesser length. For example, elastic elements can extend along the upper waist portion and along the lower terminal edge defining in part a leg opening 34.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in an alternative embodiment, one or more separate waist bands, with or without elastic elements, can be secured to one or both of the rear and front body panels, preferably along the upper terminal edges 20, 28 thereof. Likewise, one or more separate leg bands can be secured to one or both of the rear and front body panels along the leg open portions 18, 26 adjacent the leg openings 34. Alternatively, one or both of the body panels can be formed without any elastic elements. In other embodiments, the entirety of the front and/or rear body panels are elasticized.

The various waist and leg elastic elements can be formed from rubber or other elastomeric materials. One suitable material is a Lycra® elastic material. For example, the various elastic elements can be formed of Lycra® XA Spandex 540, 740, 800, or 940 decitex T-127, T-128 or T-151 elastics available from E.I. duPont De Nemours and Company, having an office in Wilmington, Del.

Referring to FIGS. 3 and 4, each body panel 4, 6 is preferably formed as a composite, or laminate material, otherwise referred to as substrates or laminates, with an elastic core 136 sandwiched therebetween. In one embodiment, the elastic core 136 is made of an elastomeric film or nonwoven elastic or stretchable material including for example but not limited to styrenic copolymers of polyisoprene, polybutadiene or polyolefin, copolymers of polyolefins, natural or styrene butadiene rubber, polyurethanes, polyamides, polyesters, and co-extrusions/blends of the aforementioned materials. The elastic core 136 can be formed as a membrane or from the plurality of elastic strands 36, as described above. In one embodiment, two or more layers 40 are bonded to the elastic core 136, and/or each other, with various adhesives, such as hot melt, or by other techniques, including for example and without limitation ultrasonic bonding and heat pressure sealing. In one embodiment, the two layers are made of a non-woven material such as a spunbond material, a bonded carded material or other known materials. In this way, the body panels are made of a stretchable/elastic material.

It should be understood that the body panels can be made of a single layer or substrate of non-woven material, a bi-layer substrate made of non-woven materials without an elastic core, or more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel material can be secured to the elastic core, such as an elastomeric layer or elastic strands or ribbons, which have been elongated and retracted, such that the material is gathered when the elastic element(s) are relaxed. Alternatively, the material can be gathered and laminated to non-elongated elastic elements. In one preferred embodiment, the body panel includes a gathered elastic laminate made from nonwoven base sheets bonded with elongated elastic elements sandwiched therebetween.

In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along one or both of the lateral article width and the longitudinal article length. Examples of such elastomeric composite materials can include a continuous filament stretch bonded laminate (CFSBL), a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary CFSBL, NBL, SBL, and NSBL materials are described in U.S. Pat. Nos. 5,226,992, 4,981,747, 4,965,122, 5,336,545, 5,385,775, 5,514,470, 4,720,415, 4,789,699, 4,781,966, 4,657,802, 4,652,487, 4,655,760, 5,116,662 and 5,114,781, and 6,323,389, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or lateral/longitudinal stretch characteristics, or which are extensible composites. Additional waist and leg elastic elements can be added to, but are not necessarily required by, the body panels. In one embodiment, the body panel can be made of a film or non-woven that is attached, by way of adhesives or thermal bonding, to an extensible non-woven material. Alternatively, the body panel can be made of a low modulus film such as ethylene methyl acrylate (EMA).

As shown in the embodiment of FIG. 1, the entirety of the body panels 4, 6, and the crotch member 50, are elasticized, such that the entirety of each of the body panels can elongate and conform to the body of the user without any substantial spacing between the body panel and the user's body, and without the attendant bulkiness of a non-elasticized material.

In one embodiment, the body panels are breathable, cloth-like, multi-directional nonwoven laminates with stretch or extensible properties. In one embodiment, the non-woven layers are pre-necked, for example between about 10% and about 80%, in the longitudinal direction, which provides extensibility in the longitudinal direction with minimal force.

In one embodiment, the body panel members 4, 6 are made of non-woven laminates of two layers of 0.55 osy polypropylene spunbond material with elongated strands of Lycra® leg and waist elastics sandwiched between the spunbond layers and thereafter adhesively bonded. In other embodiments, two layers of 0.060 osy polypropylene spundbond material can be used. In one particular embodiment, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the Assignee of the present application. In one embodiment, the body panel material is necked in the machine direction (crotch to waist).

As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micro-pleats.

In this way, the body panel can be elongated in both the longitudinal and lateral direction to conform to the body of the user when the garment is applied thereto. In particular, as the user pulls the garment up over their hips, the non-woven laminate body panels stretch in the lateral direction while the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements, incorporated in one embodiment, will increase. The body panel non-woven material is preferably substantially hydrophobic, which may optionally be treated with a surfactant or otherwise processed to impart a desired level of wettability and hydrophilicity.

The crotch member 50 of the various undergarments connecting the front and rear body panels 4, 6 can be folded such that the side edges 30, 32 of the front and rear body panels 4, 6 are aligned, whereinafter they can be fixedly secured at a seam to form the leg opening 34. The seam can be formed by bonding, sewing or otherwise attaching the side edges. Alternatively, the product can remain "open," wherein the body panels are releasably secured with one or more fastening members (not shown).

In one embodiment, the garment includes a combination of side edges that are secured to form a seam and fastening members that allow the fit of the undergarment to be adjusted. For example, in one embodiment, fastening members are preferably attached to the front body panel and extend inboard relative to the outboard side edge of the front body panel from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. In one embodiment, the fastening members are secured to the garment-side surface of the body panel.

It should be understood that, in other embodiments, the fastening members can be secured to the rear body panel and engage the front body panel or, conversely, can be secured to the front body panel and engage the rear body panel, preferably along at least a portion that is not elasticized. In one embodiment, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into a disposable absorbent undergarment, the fastening members can include a refastenable portion, such as an array of hook members, adhesives, such as pressure sensitive adhesives, buttons, zippers, snaps and other releasable and reattachable fastening devices. In various embodiments, the fastening member includes one, two or more than two tab members. In one embodiment, the fastening members comprise a carrier member, which is preferably fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Referring to the embodiments of FIGS. 1–7, the crotch member 50, otherwise referred to as an absorbent insert, is formed as a separate subassembly connected to either the bodyside or garment side surface 10, 12 of the body panel members 4, 6. Various garments having a "three-piece" construction including a front and rear body panel connected with an absorbent insert include for example and without limitation Depend® Refastenable Underwear and certain sizes of Depend® Protective Underwear, available from Kimberly-Clark Worldwide Corporation, the assignee of the present application. In either embodiment, the crotch member 50 has first and second opposed terminal end edges 60, 62. The crotch member 50 bridges the gap between the terminal edges 14, 22 of the body panels 4, 6 and is connected respectively to those body panels with an adhesive at first and second adhesive regions 88, 100.

In particular, the crotch member 50 has first and second end portions 102, 104 that overlap the front and rear body panels 4, 6 respectively and are connected thereto with the adhesive at the adhesive regions 88, 100. In one embodiment, the entirety of the end portions 102, 104 of the crotch member that overlaps the body panels can be attached thereto. The crotch member 50 can be secured to the body panels when they are in a stretched or unstretched condition.

In one embodiment, the second adhesive region 100 extends along at least the intersection of the absorbent insert 50 with the respective front and rear body panels 4, 6. It should be understood that the second adhesive region 100 may be formed between the absorbent insert and only one of the front and rear body panels, or between the absorbent insert and both of the front and rear body panels. In one embodiment, the second adhesive region extends continuously across the entirety of the lateral width of the absorbent insert between the side edges thereof. In various embodiments, the second adhesive region is formed as a bead or microswirl pattern, across the lateral width of the absorbent insert between the side edges thereof 108, 110. In one embodiment, the first adhesive was initially applied to the absorbent insert, while the second adhesive was initially applied to the body panels, with the absorbent insert and body panels then being joined.

Alternatively, the second adhesive region may extend along only a portion of the lateral width of the absorbent insert. For example, the second adhesive region may be formed as a discrete attachment point proximate the centerline 112 of the absorbent insert. In the various embodiments, the second adhesive region is formed by a continuous or intermittent swirl pattern, a line of adhesive, such as a bead, a pattern of dots of adhesive, or in some other fashion.

In a preferred embodiment, the second adhesive region 100 is formed adjacent or proximate the terminal crotch edge of the respective body panels, for example from between 0 and 0.50 inches (1.27 cm) from the terminal edge, and in one embodiment from between about 0.125 (0.3175 cm) and 0.25 inches (0.635 cm). In one embodiment, a bead of adhesive 100 was formed approximately 0.25 inches (0.635 cm) from the terminal crotch edge 14 of only the front body panel across the entirety of the width of the absorbent insert.

In other embodiments, second adhesive regions can be formed at other locations between the absorbent insert and both panels, for example adjacent the terminal edge of the absorbent insert, adjacent the side edges thereof, along the longitudinally extending centerline of the absorbent insert, or at any other location between the absorbent insert and the body panels. It also should be understood that more than two adhesive regions may be formed, for example a third adhesive region may be formed using an adhesive having a basis weight different than the first and second basis weights, or which has different peel strength properties than adhesives in the first and second adhesive regions. Of course, additional adhesive regions may be formed as needed. It should be understood that the term adhesive region does not mean an area of adhesive that is contiguous, but rather refers to various areas of adhesive, whether contiguous or disconnected, that have similar basis weights and/or properties, e.g., peel strengths.

Referring to the embodiments of FIGS. 1 and 4–8, the remainder of the overlapping portion of the end portions 102, 104 of the absorbent insert and the front and rear body panels 4, 6 are connected with a first adhesive region 88. The first adhesive region can be formed as a continuous application of adhesive. In various embodiments, the first adhesive region is formed as one or more lines of adhesive, swirls, discrete points, etc. For example, a plurality (meaning two or more) of discrete attachment locations can extend in the longitudinal direction along the entire length of the overlapping portion of the crotch member, along only a portion of the length, or at a discrete point. In another embodiment (not shown), the first adhesive region can be formed from a plurality of discrete attachment locations spaced laterally across the width of the absorbent insert. In other embodiments, the first adhesive region can include any number of attachment patterns, including for example and without limitation securing the absorbent insert along its side edges, along its terminal edges, along the peripheral edges, along a centerline, along various diagonals or cross-hatchings, at a pattern of dots, swirls, etc., or some combination thereof.

In one embodiment, the first adhesive region 88 includes an adhesive having a basis weight of between about 5 gsm and about 15 gsm (grams per square meter), and in one embodiment between about 5 gsm and about 10 gsm. In one particular example, an adhesive having a basis weight of approximately 7 gsm was intermittently applied over a first adhesive region covering the entirety of the overlapping region between the end portions of the absorbent insert and the front and rear body panels. One suitable adhesive is National Starch 5610 adhesive available from National Starch and Chemical Company, located in Berkeley, Calif.

In one embodiment, the second adhesive region 100 includes an adhesive having a basis weight of between about 20 gsm and about 50 gsm. In one particular example, the adhesive in the second adhesive region had a basis weight of approximately 30 gsm. In some embodiments, the second adhesive region overlaps areas of application of the first adhesive region, or there is a feathering therebetween. In particular, the second adhesive 100 was applied as an intermittent bead approximately 0.0 to 0.50 inches (1.27 cm), alternatively 0.125 (0.3175 cm) to 0.50 inches (1.27 cm), and alternatively 0.25 inches (0.635 cm), from the terminal crotch edge of the front body panel.

Various samples of absorbent inserts attached to body panels with adhesive were tested for peel strength in the cross-direction 502 and machine direction 500.

Figure 10:
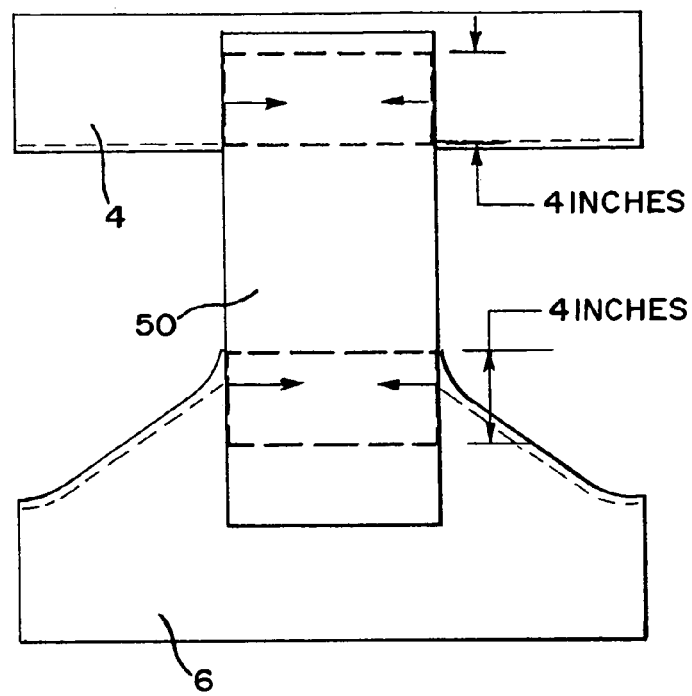
FIG. 10 is a schematic representation of the sample procurement for a cross-direction peel strength test.
Figure 11:
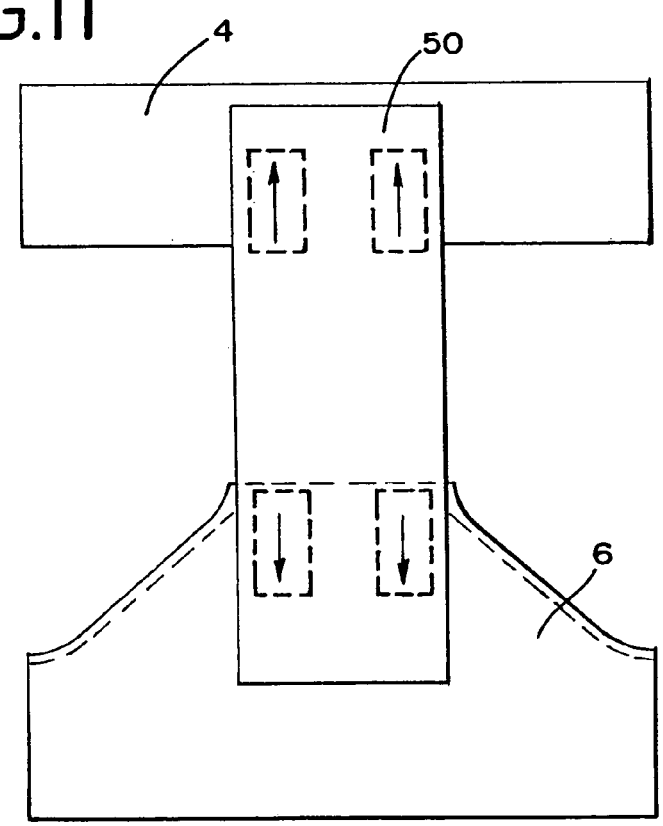
FIG. 11 is a schematic representation of the sample procurement for a machine-direction peel strength test.

Sample:

In a first sample, shown in FIGS. 8, 10 and 11, the front body panel 4 included 18 strands of 620 decitex (dtex) lycra elongated to 250% sandwiched between two 9.75 inch (24.765 cm) wide layers of 0.55 osy spunbond, corresponding to a large size garment. The waist elastics 36 were spaced 6 mm apart and begin 9 mm from the front edge 20. Five front leg elastics spaced 3 mm apart and including 940 dtex Lycra elongated to 250% run straight along the leg opening portions beginning approximately 9 mm from the leg opening portion 18. Adhesive was pulsed over a width of 1.5 inches (3.81 cm) and a length of 8.38 inches (21.2852 cm) along the crotch portion 16. This allows the leg elastics to be cut and snapped so they leave an opening for placement of the absorbent insert.

The rear body panel 6 included 29 strands of 620 dtex lycra elongated to 250% sandwiched between two 15 inch (38.1 cm) wide layers of 0.55 osy spunbond, corresponding to a large garment respectively. The waist elastics are spaced 6 mm apart and begin 9 mm from the front edge (20). Six back leg elastics spaced 3 mm apart and including of 940 dtex Lycra elongated to 250% run in a pre-defined pattern which matches the leg opening portions 26 of the rear body panel Adhesive is also pulsed over a width of 1.5 inches (3.81 cm) and a length of 8.38 inches (21.2852 cm) along the crotch portion 24. This allows the leg elastics to be cut and snapped so they leave an opening for placement of the absorbent insert.

A 21 inch (53.34 cm) by 8.38 inch (21.2852 cm) absorbent insert was secured to the front and rear body panels with an adhesive. The length of the adhesive overlap on the front body panel was 4.59 inches (11.6586 cm), while the length of the adhesive overlap on the rear body panel was 7.16 inches (18.1864 cm). The absorbent insert included a topsheet (10 inches (25.4 cm) slit down to 8.38 inches (21.2852 cm)) adhered to a surge layer (11 inches (27.94 cm) by 3.66 inches (9.2964 cm)), which was adhered to a wrapsheet overlying an absorbent core (19 inches (48.26 cm) by 5 inches (12.7 cm)), which was adhered to a BSTL backsheet (10 inches (25.4 cm) slit down to 8.38 inches (21.2852 cm)).

Peel Strength Tests:

Cross Direction Test:

The cross-direction peel test measures data using a Sintech measurement device (Model # MTS-Sintech 1S— (Serial # 1S/042895/148). Arrows in each testing area, shown in FIG. 10, indicate the direction of peel used in testing. The following parameters can be used to duplicate test data.

Test Equipment
Load Cell—25 lb.
Test Grips—4 inches

Sample Preparation
1) Cut sample from the back or front body panel beginning at the crotch edge and extending 4 inches (10.16 cm) from the crotch edge. The width of the sample corresponds to the width of the absorbent insert, e.g. 8 inches in one embodiment.
2) Place masking tape along the unattached edge of the insert (right and left side) to make the insert edge portion long enough to position in the grips on the Sintech measurement device.
3) Place ½ inch (1.27 cm) of the insert edge with the masking tape attached in the top jaw of the sintech testing machine.
4) Place the spunbond back or front panel into the bottom jaw of the sintech testing machine ensuring that the gm reading is between 0–10.
5) Peel the insert from the back or front panel on each side of the product. Test all the right side samples first then the left side (Right & left sides are identified as if the pant were being worn).

Test Inputs
Cross Head Speed—10.0 inches/min
Gauge Length—2.0 inches
Calculation Start Point—0.5 inches
Calculation End Point—4.5 inches
End of Test—5.0 inches Test Outputs
Average Load (grams)
Peak Load (grams)
Energy (gram-centimeter)

Machine Direction Test:

The machine direction peel test measures data using a Sintech measurement device (Model # MTS-Sintech 1S— (Serial # 1S/042895/148). Arrows in each testing area, shown in FIG. 11, indicate the direction of peel used in testing. The following parameters can be used to duplicate test data. The programming sequence is set forth at Appendix 1.

Test Equipment
Load Cell—25 lb.
Test Grips—4 inches

Sample Preparation
1) Mark the edge of the adhesive along both sides of the insert with a pen or marker (front and back if testing both ends of the product).
2) Cut a 3 inch (7.62 cm) wide sample from the right and left side of the product (make sure the sample is cut to the inside of the adhesive mark to ensure a sample with a 3 inch (7.62 cm) sample of adhesive). The sample is cut in the Machine Direction of the Insert (waist to crotch direction-see FIG. 11). The sample was further cut to a 10 inch (25.4 cm) length, although the length is not critical so long as it exceeds the travel of the testing apparatus.
3) Remove the absorbent material from the 3 inch (7.62 cm) sample so as to expose the backsheet.
4) Place ½ inch (1.27 cm) of the front or rear panel in the top jaw of the sintech testing machine. If the front or rear body panel is not long enough you may need to add masking tape to extend the length.
5) Place the backsheet of the absorbent insert in the bottom jaw of the sintech testing machine ensuring that the gm reading is between 0–10.
6) Peel the insert from the front or rear panel using the following settings.

Test Inputs
Cross Head Speed—10.0 inches/min
Gauge Length—2.0 inches
Calculation Start Point—0.5"
Calculation End Point—4.5"
End of Test—5.0"

Test Outputs
Average Load (grams)

Test Outputs
Average Load (grams)
Peak Load (grams)
Energy (gram-centimeter)

In a first testing sequence, machine-direction peel strength test was performed on ten (10) samples of the above article as set forth in Tables 1 and 2 with some modification to the test inputs.

TABLE 1

|   | Peak Load Gm | Avg Ld Gm |
|---|---|---|
| 1 | 1557.4 | ****** |
| 2 | 1027.5 | 522.2 |
| 3 | 1393.8 | 597.8 |
| 4 | 1548.2 | 666.2 |
| 5 | 1163.4 | 573.5 |
| Mean | 1338.1 | |
| Min | 1027.5 | |
| Max | 1557.4 | |
| Stdv | 235.7 | |
| % Cov | 17.6 | |

Specimen Comments:
Test Inputs:
Crosshead Speed    12.00 In/Min
Load Limit HI      1000 Gm
Test End           4.50 In

TABLE 2

|   | Peak Load Gm | Avg Ld Gm |
|---|---|---|
| 1 | 1428.4 | 865.0 |
| 2 | 1184.2 | 554.7 |
| 3 | 1087.4 | 550.0 |
| 4 | 1181.9 | 720.2 |
| 5 | 1368.5 | 738.3 |
| Mean | 1250.0 | 685.6 |
| Min | 1087.4 | 550.0 |
| Max | 1428.4 | 866.0 |
| Stdv | 142.5 | 133.9 |
| % Cov | 11.4 | 19.5 |

Specimen Comments:
Test Inputs:
Crosshead Speed    12.00 In/Min
Load Limit HI      1000 Gm
Test End           4.50 In Next, samples were made that included a bead of secondary adhesive. In particular, for samples 1–5 (Table 3), a bead of adhesive (Findley 2717) was applied between the rear body panel along the crotch edge thereof using a Nordson Summit applicator (Nordson ES 400 Electric Applicator and drive with a Summit two orifice nozzle). For samples 6–11, a bead of adhesive was applied between the front body panel along the crotch edge thereof using a Nordson Bead applicator (UM 400 Universal application with Nordson SATURN precision nozzle 322424 (with 0.024 inch (0.06096 cm) opening)).

The machine-direction peel strength test was performed on eleven (11) samples of the above article as set forth in Table 3 with some modification to the test inputs.

TABLE 3

|   | Peak Load Gm | Avg Ld Gm |
|---|---|---|
| 1 | 6354.2 | ****** |
| 2 | 7893.4 | ****** |
| 3 | 6460.7 | ****** |
| 4 | 6881.5 | ****** |
| 5 | 7872.1 | ****** |
| 6 | 7962.7 | 2054.0 |
| 7 | 5773.6 | 1370.2 |
| 8 | 7643.1 | 1266.0 |
| 9 | 7004.0 | 1262.0 |
| 10 | 7579.2 | 1513.8 |
| 11 | 6684.4 | 2061.6 |
| Mean | 7100.8 | 1587.9 |
| Min | 5773.6 | 1262.0 |
| Max | 7962.7 | 2061.6 |
| Stdv | 738.1 | 375.3 |
| % Cov | 10.4 | 23.6 |

Figure 14:
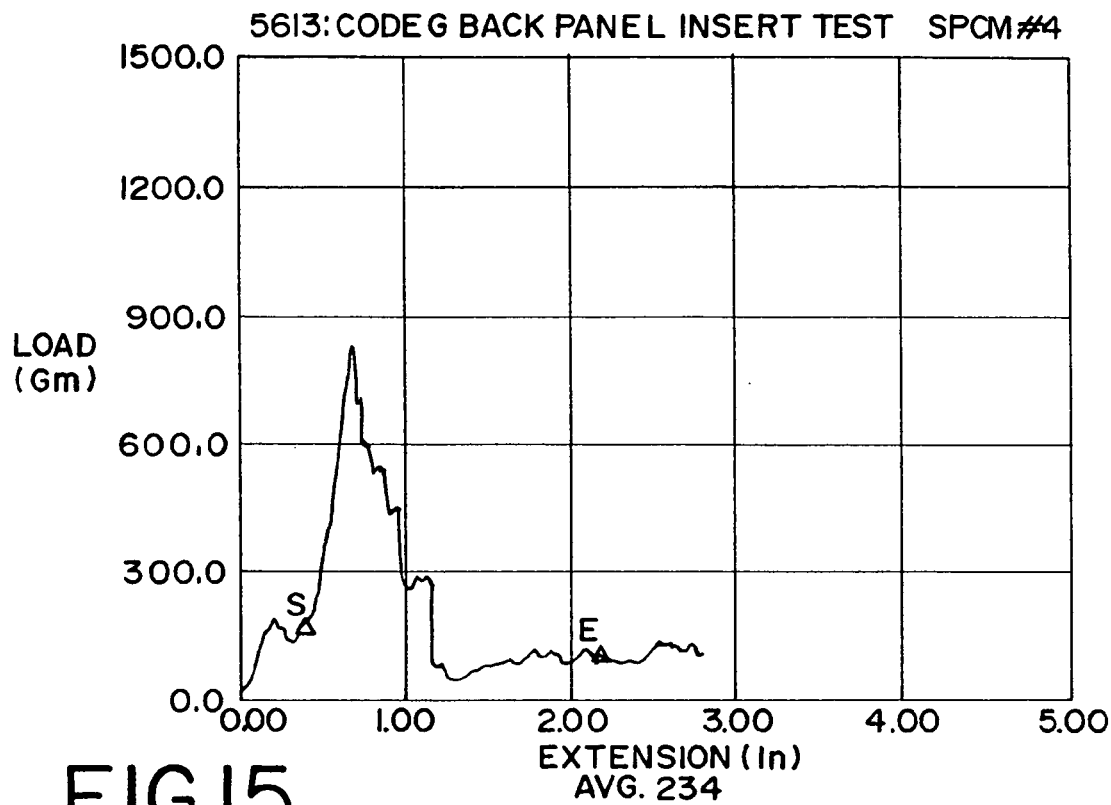
FIG. 14 is a load v. extension graph for a machine direction peel strength test.
Figure 15:
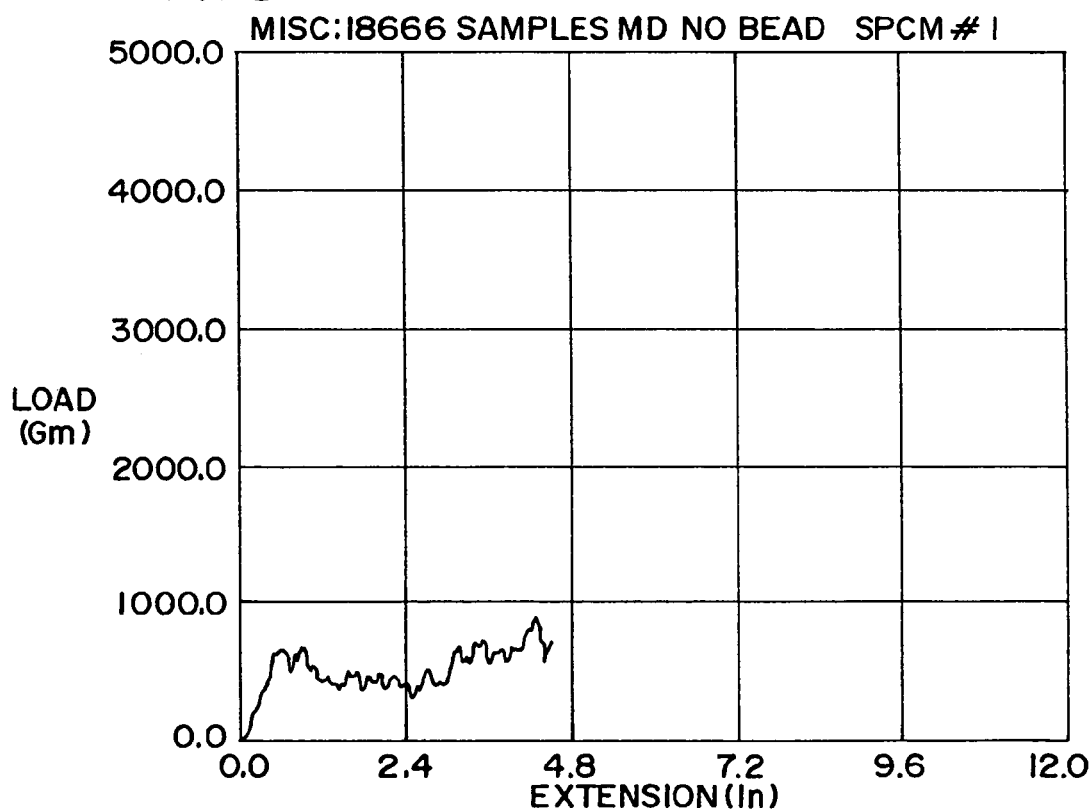
FIG. 15 is a load v. extension graph for a machine direction peel strength test.
Figure 16:
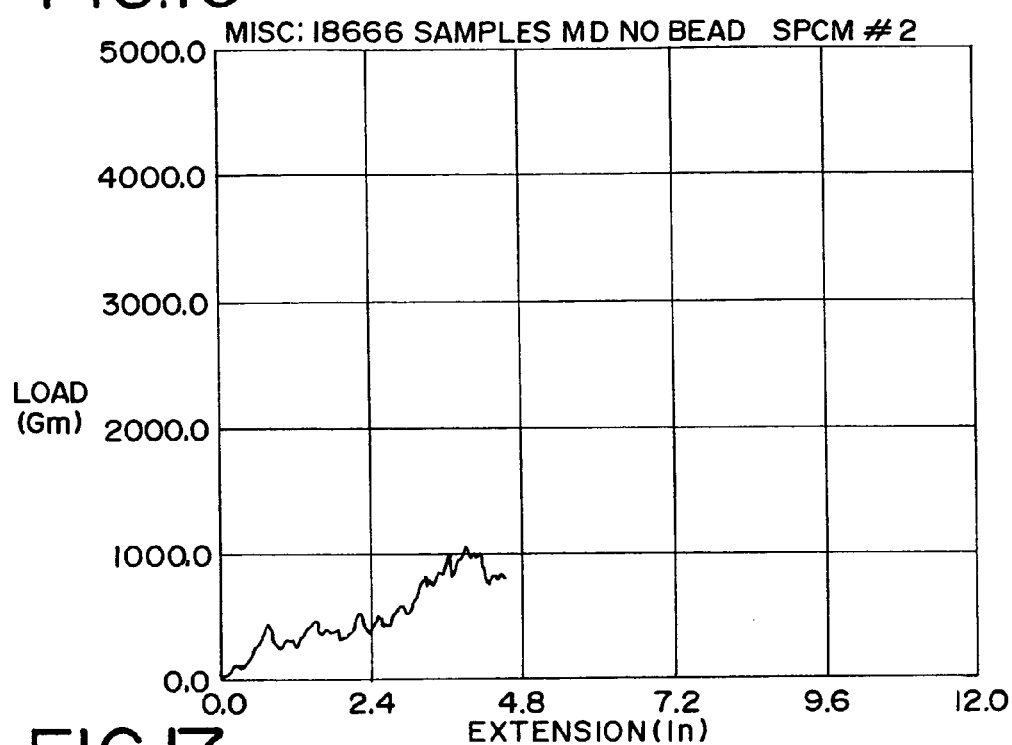
FIG. 16 is a load v. extension graph for a machine direction peel strength test.
Figure 17:
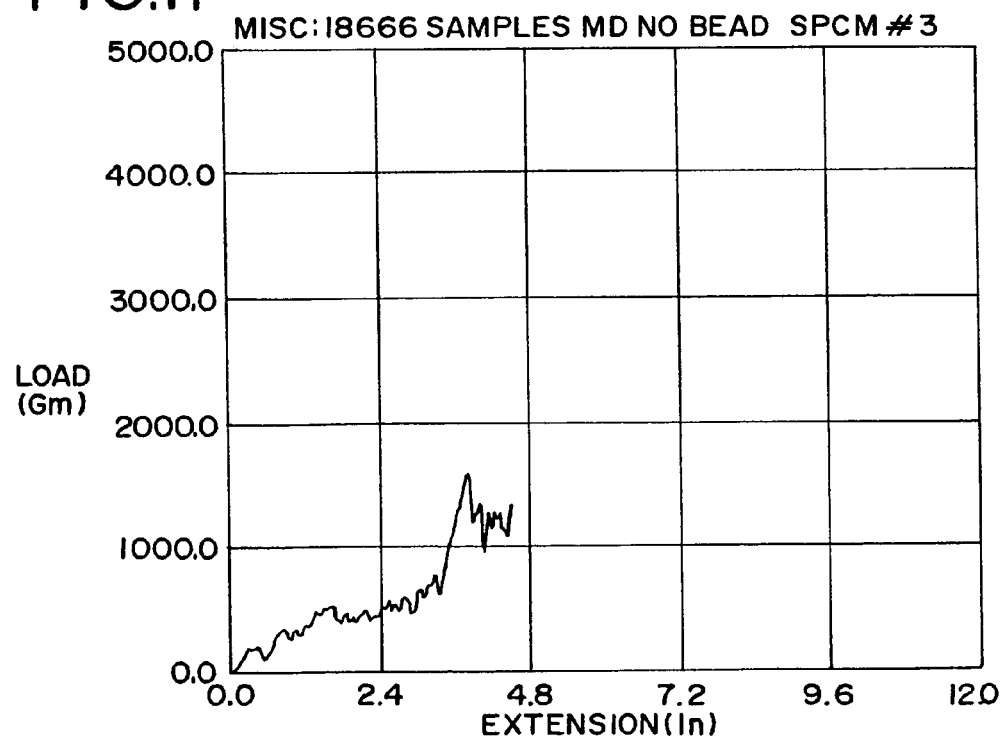
FIG. 17 is a load v. extension graph for a machine direction peel strength test.
Figure 20:
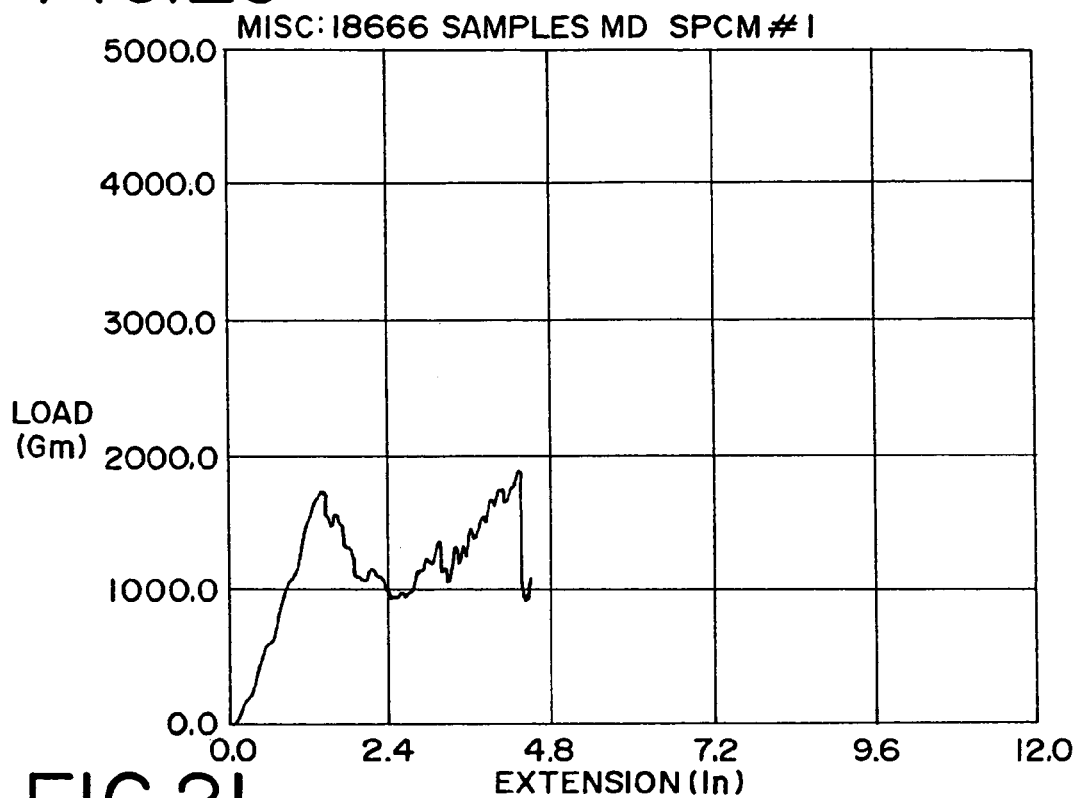
FIG. 20 is a load v. extension graph for a machine direction peel strength test.
Figure 21:
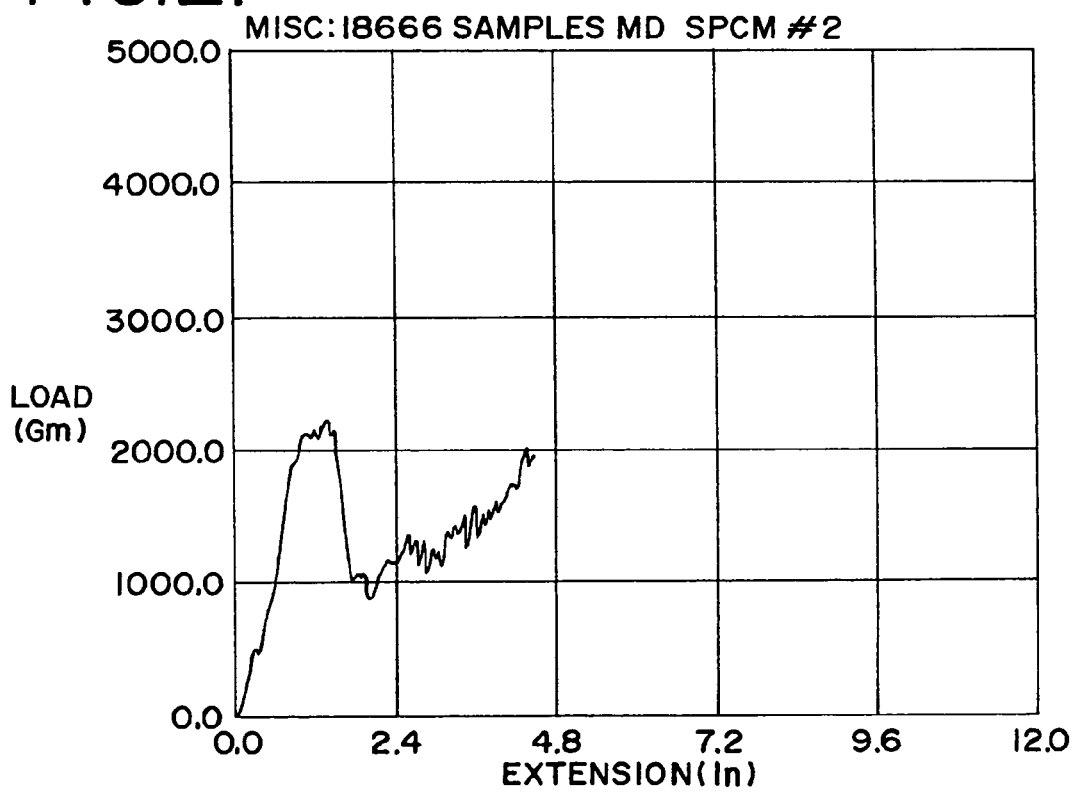
FIG. 21 is a load v. extension graph for a machine direction peel strength test.
Figure 22:
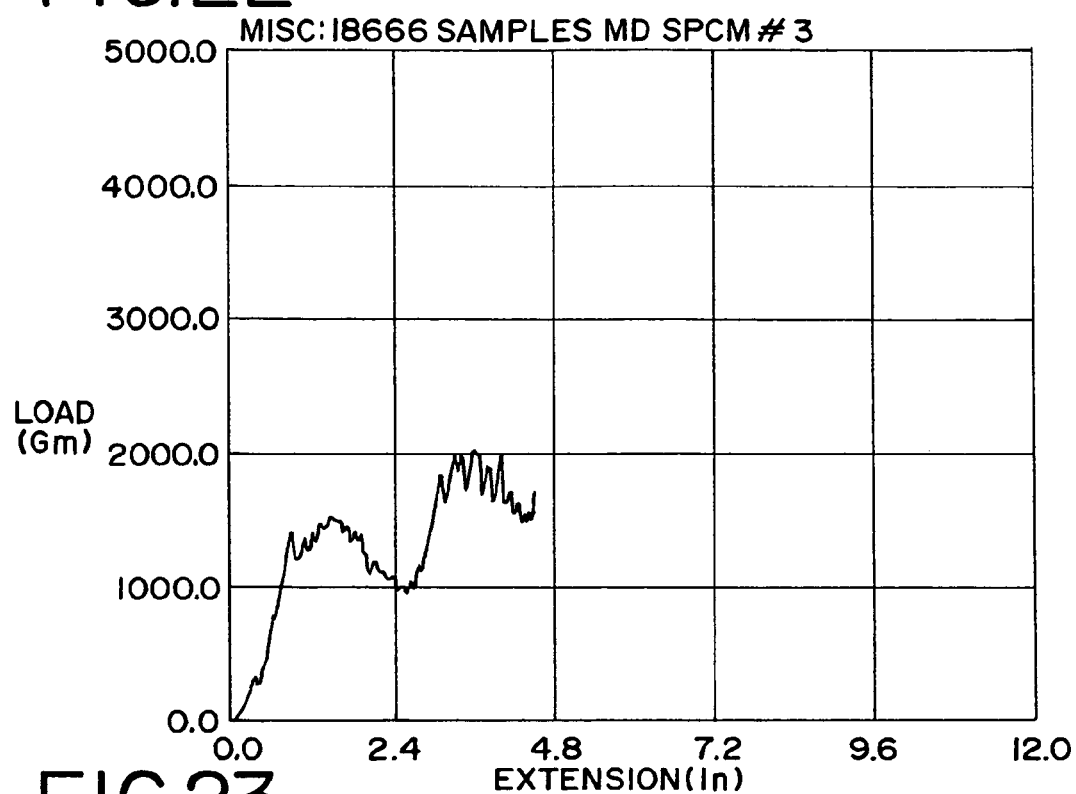
FIG. 22 is a load v. extension graph for a machine direction peel strength test.
Figure 23:
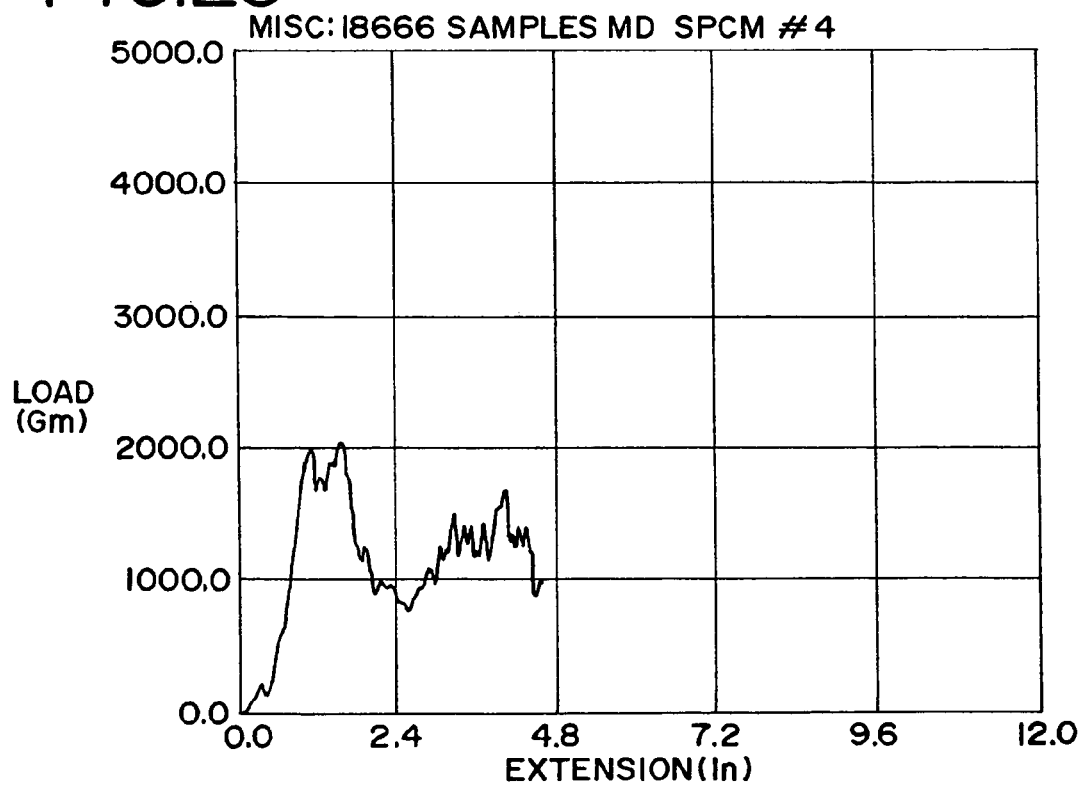
FIG. 23 is a load v. extension graph for a machine direction peel strength test.
Figure 24:
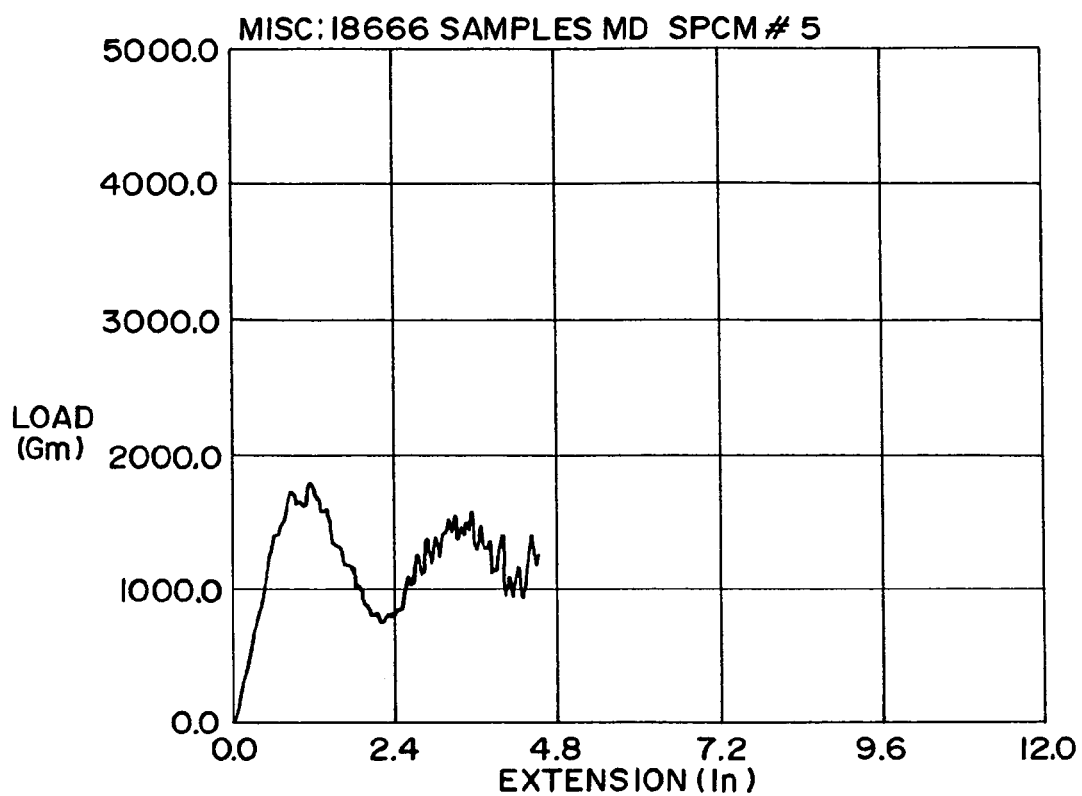
FIG. 24 is a load v. extension graph for a machine direction peel strength test.

Specimen Comments:
1: Samples 1–5 Back Summit only
6: 6–10 Front Panel bead - All material failures
Test Inputs:
Crosshead Speed    12.00 In/Min
Load Limit HI      12000 Gm
Test End           3.25 In In another machine direction peel strength testing sequence, four (4) additional samples were modified to include a bead of secondary adhesive. In particular, a bead of adhesive was applied between the rear body panel along the crotch edge thereof using a Nordson Bead applicator. The average load for the peel test is set forth in Table 4 with some modification to the test inputs. In addition, the load v. extension for sample 1, 3 and 4 is shown in FIGS. 12–14. The bead in Sample 2 was not properly formed and the data point is not considered as being valid. Moreover, the integrity of the beads in samples 1, 3 and 4 was not uniform.

TABLE 4

|   | Avg. Load Gm |
|---|---|
| 1 | 280.5 |
| 2 | 77.8* |
| 3 | 140.3 |
| 4 | 234.1 |
| Mean | 183.2 |
| Min | 77.8 |
| Max | 280.5 |
| Stdv | 91.3 |
| % Cov | 49.9 |

Specimen Comments:
Test Inputs:
Crosshead Speed    500.00 mm/Min
Load Limit HI    5 Kg
Test End    3.20 In
*This is considered a bad data point.

In yet another testing sequence, with test inputs as shown in Appendix 1, machine-direction peel strength test was performed on five (5) samples of the above article as set forth in Table 5. The samples were quite old, and there may have been some degradation of the adhesive. Load v. extension was plotted for each sample in FIGS. 15–19.

TABLE 5

|   | Peak Load Gm | Avg Ld Gm |
|---|---|---|
| 1 | 881.4 | 483.8 |
| 2 | 1063.1 | 470.9 |
| 3 | 1603.6 | 555.7 |
| 4 | 926.3 | 378.5 |
| 5 | 1399.5 | 527.5 |
| Mean | 1174.8 | 483.3 |
| Min | 881.4 | 378.5 |
| Max | 1603.6 | 555.7 |
| Stdv | 314.1 | 67.7 |
| % Cov | 26.7 | 14.0 |
| Median | 1063.1 | 483.8 |

Next, five samples were made that included a bead of secondary adhesive. In particular, for samples 1–5 (Table 6), a bead of adhesive (Findley 2717) was applied between the rear body panel along the crotch edge thereof using a Nordson Bead applicator. The machine-direction peel strength test was performed on the five samples of the above article as set forth in Table 6 with some modification to the test inputs. The samples were quite old, and there may have been some degradation of the adhesive. Load v. extension was plotted for each sample in FIGS. 20–24.

TABLE 6

|   | Peak Load Gm | Avg Ld Gm |
|---|---|---|
| 1 | 1904.2 | 1113.6 |
| 2 | 2227.1 | 1310.0 |
| 3 | 2029.8 | 1246.1 |
| 4 | 2047.7 | 1125.6 |
| 5 | 1812.2 | 1168.0 |
| Mean | 2004.2 | 1192.7 |
| Min | 1812.2 | 1113.6 |
| Max | 2227.1 | 1310.0 |
| Stdv | 157.4 | 83.6 |
| % Cov | 7.9 | 7.0 |
| Median | 2029.8 | 1168.0 |

In other embodiments, the front body panel 4 includes 13 strands of 940 dtex lycra elongated to 250% sandwiched between two 8.50 inch (21.59 cm) wide layers of 0.55 osy spunbond, corresponding to a Small/Medium size garment. The rear body panel 6 includes either 24 strands of 940 dtex lycra elongated to 250% sandwiched between two 13.75 inch (34.925 cm) or 15 inch (38.10 cm) wide layers of 0.55 osy spunbond, corresponding to the Small/Medium size garment.

In various embodiments, and referring to Tables 1 and 2, the first adhesive region 88 has a machine-direction peel strength with a mean peak load of between about 1000 grams and about 2000 grams, alternatively between about 1200 grams and about 1400 grams and alternatively between about 1250 grams and about 1338 grams. The first and second adhesive regions 88, 100 in combination have a peel strength with a mean peak load of between about 5000 grams and about 10,000 grams, alternatively between about 6,500 grams and about 7,500 grams, alternatively between about 5000 and 7200 grams and alternatively about 7100 grams. It should be understood that different peel strengths can be achieved using adhesives that have the same basis weight. Referring to FIGS. 12–14, the mean peak load in the machine direction was between about 450 grams and about 900 grams. In various embodiments, the mean peak load for peel strength in the machine direction is between about 300 grams about 1100 grams.

In various embodiments, and referring to Tables 1 and 2, the first adhesive region 88 has a machine-direction peel strength with a mean average load of between about 400 grams and about 1000 grams and alternatively between about 500 grams and about 900 grams. Referring to Table 3, the first and second adhesive regions 88, 100 in combination have a peel strength with a mean average load of between about 500 grams and about 2,200 grams, alternatively between about 1,200 grams and about 2,000 grams and alternatively between about 1,300 and 1,700 grams. Referring to Table 4, the machine-direction peel strength has a mean average load of between about 100 and 300 grams and alternatively between about 150 and about 250 grams.

Referring to Table 5, and FIGS. 15–19, in various embodiments, the first adhesive region 88 has a machine-direction peel strength with a mean peak load of between about 800 and about 1500 grams, alternatively between about 1000 and about 1200 grams and alternatively about 1175 grams. The first adhesive region 88 has a mean average load of between about 350 grams and about 1000 grams, alternatively between about 400 grams and about 600 grams and alternatively about 485 grams.

Referring to Table 6, and FIGS. 20–24, the first and second adhesive regions 88, 100 in combination have a machine-direction peel strength with a mean peek load of between about 1500 and about 2500 grams, alternatively between about 1800 and about 2200 grams and alternatively about 2000 grams. The first and second adhesive regions in combination have a mean average load of between about 1000 grams and about 1500 grams, alternatively between about 1100 grams and about 1350 grams and alternatively about 1200 grams.

Accordingly, in various embodiments, the first adhesive region 88 has a machine-direction peel strength with a mean peak load of less than about 1500 grams, and a mean averageload of less than about 500 grams. Conversely, the first and second adhesive regions 88, 100 in combination have a machine-direction peel strength with a mean peak load of greater than about 1500 grams and alternatively greater than about 2000 grams, and a mean average load of greater than about 500 grams and alternatively greater than about 1000 grams.

It should also be understood that the term adhesive region also refers to two or more components being joined by ultrasonic bonding, thermal bonding, pinning, stitching, or any other attachment techniques know in the art, as well as combinations thereof. Therefore, for example, the crotch member can be joined to the body panel with two different ultrasonic bonding patterns at the first and second adhesive regions, which would provide in one embodiment two different peel strengths.

In one embodiment, shown in FIGS. 1–4, the crotch member is configured as an absorbent insert 50, which includes a substantially liquid permeable top sheet 64, or liner, and a substantially liquid impermeable back sheet 66. A retention portion 70 is disposed or sandwiched between the topsheet and the backsheet, which are connected. It should be understood that the term "absorbent insert" refers to any material or assembly capable of absorbing liquids or bodily exudates, and may be formed from a single material or component, for example a retention portion, or can be formed as a composite of several components. It should also be understood that the term "crotch member" refers to any member of any material, including for example and without limitation those described herein with respect to the body panels and absorbent inserts, and is not limited to absorbent inserts and/or materials. For example, the crotch member may be made of one or more layers of a non-woven material. It should further be understood that when the crotch member does not include an absorbent material, it can still be used in conjunction with various disposable absorbent pads such as adult incontinent and/or feminine pads so as to improve the performance and comfort of those pads by maintaining them in close proximity to the body of the user.

Referring to FIGS. 1–4, the top sheet 64, back sheet 66 and other components of the absorbent insert can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein.

In one embodiment, one or more crotch elastic members 38 are sandwiched between the top sheet 64 and backsheet 66 along the side edges thereof. The elastic members 38 can extend the entire longitudinal extent of the absorbent insert, or along only a portion thereof. Additional layers, including for example, a liquid acquisition and distribution layer 72, also referred to as a surge or transfer layer, are also preferably incorporated into the absorbent insert. In one embodiment, the transfer layer does not run the entire length of the absorbent insert and is shorter than the retention portion.

In one embodiment, the retention portion 70, transfer layer 72 and other components, such as tissue layers 74, 75, are free floating (unattached) between the back sheet 64 and the top sheet 66, which are secured along only the peripheral edges thereof. Alternatively, the retention portion 70, transfer layer 72 and other components are minimally attached to one or both of the back sheet 66 and top sheet 64. For example, the retention portion can be secured to the back sheet along an attachment location positioned along the longitudinal centerline 112 of the retention portion. Alternatively, or in combination with the back sheet connection, the transfer layer or retention portion can be minimally attached to the top sheet. In this way, the retention portion 70, transfer layer 72 and other components do not impede or substantially affect the lateral stretchability and extensibility of the absorbent insert 50 and in particular the top sheet and back sheet, at least one of which is secured to the body chassis.

In another alternative embodiment (not shown), the retention portion is secured along the centerline at a point midway between the two ends of the retention portion. In this embodiment, the retention portion also does not restrict or impede the stretchability and extensibility of the absorbent insert, and in particular the top sheet and back sheet, in the lateral or longitudinal directions 500, 502.

In other embodiments, the top sheet is indirectly joined to the backsheet by affixing the topsheet to intermediate layers, such as the surge layer or retention portion, which in turn is affixed to the backsheet. The absorbent insert also may include barrier cuffs, or leakage control shields, formed along the opposite longitudinally extending edges of the absorbent composite.

In one embodiment, the back sheet 66 is a stretchable, elastic, liquid impervious member. Alternatively, the back sheet may be liquid permeable, e.g., when an additional barrier layer is used with the retention portion. In one embodiment, shown in FIGS. 1–4, the back sheet 66 is a laminate structure made of a stretchable, elastic material, such as an elastomeric film 80, which is laminated to an extensible non-woven material layer 82. It should be understood that the backsheet can be formed from a single layer or substrate or more than two layers or substrates. The backsheet can be stretchable in both the lateral and longitudinal direction, or be stretchable in one direction and extensible in the other.

The backsheet 66 prevents various bodily fluids and exudates from wetting or otherwise contaminating various bedding or outer garments worn by the user over the absorbent garment. The backsheet can be made of the same materials described above in connection with the body panels. In one embodiment, the backsheet can include a film, which can be made of the various materials described above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance. In one embodiment, the absorbent insert includes a breathable stretch thermal laminate (BSTL), which includes a liquid impermeable film thermally bonded to a permeable non-woven material.

In various embodiments, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 millibars substantially without leakage. The backsheet member can alternatively support a hydrohead of at least about 55 millibars, and optionally, can support a hydrohead of at least about 60 millibars, or more, to provide improved benefits.

In one example, the backsheet can be composed of a necked fiber, a creped fiber, a micro-pleated fiber, polymer films or the like, as well as combinations thereof. The fabrics may be woven or nonwoven materials, such as spunbond fabrics.

In various constructions, the top sheet 64 can include various woven or nonwoven materials and laminates, which can be stretchable or extensible. In one embodiment, the top sheet 64, shown in FIGS. 2–4, is an extensible material, such as a necked spunbond material. For example, the topsheet can be composed of a meltblown or spunbonded web of desired fibers, and may also be a bonded-carded web. For example, the topsheet and liner can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like. In another embodiment, the top sheet can also include an elastic material, such that it is stretchable.

The retention portion 70 is made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C., or alternatively Dow 2035 available from Dow Chemical Co., Midland Mich. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion preferably can be made of a single or dual layer of absorbent material. In one embodiment, the retention portion has an hour-glass shape with enlarged end regions. Alternatively, the retention portion is substantially rectangular. The retention portion can include a folded or multi-layered configuration. Likewise, the entire absorbent insert can have a folded configuration, with various folds formed from one or more of the backsheet, top sheet, retention portion or other components. The retention portion can have a length substantially equal to, or slightly shorter than, the length of the absorbent insert. The retention portion can include one or more barrier layers attached to the absorbent material. In one embodiment, an upper tissue substrate 74 is disposed adjacent the retention portion. Alternatively, a lower tissue substrate 75 can be disposed adjacent an opposite side of the retention portion, or the tissue can completely envelope the retention position, or can envelope a portion thereof, for example by way of a C-shaped upper tissue layer.

Referring to FIGS. 1 and 5–8, a method of assembling the absorbent garment includes positioning the rear body panel 6 relative to the front body panel 4 such that the terminal crotch edge 22 of the rear body panel is longitudinally spaced from and forms a gap 116 with the terminal crotch edge 14 of the front body panel. Adhesive is applied to one or both of the body panels and absorbent insert at the first and second adhesive regions 88, 100. The adhesive can be applied using a bead applicator or a summit applicator. In various embodiments, the adhesive may be applied as a meltblown, meaning a material that is formed from the random spray of a molten polymer, as a swirl spray, meaning an adhesive pattern with a twisting shape or mark (usually induced by hot air impingement), as a slot coat, meaning a coating method similar to extrusion, as an extrusion, meaning that the material is expelled through an orifice (typically with the applicator resting or touching the material the adhesive is being applied to), and/or as a control coat application.

In various embodiments, the primary and secondary adhesive was applied as shown in Table 7 and FIG. 8. In particular, the primary adhesive is applied to a continuous web assembly of a plurality of absorbent inserts 50 moving in a first machine direction. The adhesive is applied intermittently for an adhesive on length (Laon), wherein the adhesive is applied to the end portions of successive absorbent inserts prior to their separation along a perforation line 103 and an adhesive off length (Laoff). The adhesive is applied across the entirety of the width (W) of the absorbent insert. Various on and off lengths are set forth in Table 7.

The secondary adhesive is applied to the body panels moving in a second machine direction along the terminal crotch edges thereof, preferably in a bead formation. It should be understood, the length of the secondary bead corresponds to and is in the same direction as the width of the primary adhesive, while the width corresponds to and is in the same direction as the length of the primary adhesive. The secondary adhesive is applied intermittently to the body panels for add on lengths and off lengths as set forth in Table 7. The absorbent inserts are successively separated from each other, for example by breaking the perforation line 103 and applied to the body panels in the cross-machine direction.

TABLE 7

(Adhesive Application)

| Adhesive | Applied to | Type of Adhesive | Adhesive Add-on | Adhesive Width (W) | Adhesive "on" length (Laon) | Adhesive "off" length (Laoff) | Applicator Type |
|---|---|---|---|---|---|---|---|
| Primary Adhesive (Sample 1) | Absorbent Insert (BSTL) | National Starch 5610 | 6 to 15 gsm (Actual about 11 gsm) - target is 7 gsm | Target = 7.38" | 11.75" + or − 0.5" | 9.25" +/− 0.5" | Nordson Control Coat |
| Primary Adhesive (Sample 2) | Absorbent Insert (BSTL) | National Starch 5610 | 6 to 15 gsm - target is 7 gsm | Target = 6.75 | 9.77" +/− 0.5" | 9.25 +/− 0.5" | Nordson Control Coat |
| Secondary Adhesive (Samples 1 and 2) | Body Panel | Findley 2717 was used; (NS5610 - Alternative) | Target is 30 gsm | 1/16" to 1/4" | 6.75" or 7.38" | 22.38" or 21.75" | Nordson Summit or Bead Applicator |

In one embodiment, adhesive of a first basis weight is applied to either one or both of the body panels or the absorbent insert in the first adhesive region, and in some embodiments also to the area of the second adhesive region, while adhesive of a second basis weight is applied to the other of one or both of the body panels or the absorbent insert in the second adhesive region. In another embodiment, adhesives of both basis weights are applied to the body panel, while in another embodiment, adhesives of both basis weights are applied to the absorbent insert. The absorbent insert 50 is positioned such that it bridges the gap 116 between the terminal crotch edges 14, 22 of the front and rear body panels 4, 6 with the first and second end portions 102, 104 overlying the front and rear body panels respectively. The first and second end portions of the absorbent insert are then connected to corresponding ones of the front and rear body panels. It should be understood that only one end of the absorbent insert may be connected to the front or rear body panel with two adhesive regions, while the other end is secured with only a single adhesive region. It should also be understood that more than two adhesive regions can be provided, with adhesives of other basis weights being used to secure the absorbent insert to the body panels. In another embodiment (not shown), the absorbent insert has one end connected to a single body panel having a terminal crotch edge in the manner described herein using at least two adhesive regions. The body panel forms a belt that goes around the waist of the user.

In other embodiments, the second adhesive region can be located in locations other than along the crotch edge. For example and without limitation, the second adhesive region can be formed as various discrete points, as longitudinal extending lines or swirls and/or along the ends of the absorbent insert.

In another aspect, the manufacturer or retailer of the afore-described absorbent garments provides instructional information to the user, for example by way of textual or pictorial indicia on the packaging materials, about how the garment works. For example, the manufacturer or retailer can explain to the end user the advantages of the variable adhesive regions, and the resultant advantages associated therewith.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

APPENDIX 1

Method Description:

Peel Adhesion Developmental Method

Start of Test Messages:

Pre-Sample Messages:

Pre-Specimen Messages:

| Graphics Window, Y-Axis: | |
|---|---|
| Y Axis Scaling Max | MANUAL |
| Y Axis Scaling Min | MANUAL |
| Y-Axis Label | LOAD |
| Y-Axis units | Gm |
| Y-Axis Min | 0.000000 |
| Y-Axis Max | 5000.000000 |
| Decimals | 1 |

| Graphics Window, X-Axis: | |
|---|---|
| X Axis Scaling Max | MANUAL |
| X Axis Scaling Min | MANUAL |
| X-Axis label | EXTENSION |
| X-Axis units | In |
| X-Axis Min | 0.000000 |
| X-Axis Max | 12.000000 |
| Decimals | 1 |
| X Offset | 0.000000 |

| Test Flow: | |
|---|---|
| Method Access Level | [5] |
| Specimens per Sample | [999] |
| Speed Increment | [0.1000000] |

-continued

Test Flow:

| | |
|---|---|
| Show Graph | [Y] |
| Show Results | [Y] |
| Take Data During Pause | [N] |
| Auto Sample Increment | [N] |
| Auto Raw Data Save | [N] |
| Auto Reject on Limits | [N] |
| Auto Sample Print | [N] |
| Discard on Reject | [Y] |
| Auto Comment | [N] |
| Auto Sample Upload | [N] |
| Auto Crosshead Return | [N] |
| Gage Removal | [N] |
| Pause For Gage Removal | [N] |
| Skip Post-test Screen | [N] |

Reference Loaded: NONE

Configuration:

| | |
|---|---|
| Load Direction | UP |
| Extension Direction | UP |
| Compliance | No |
| End Of Test Action | GOTO |
| Method Type | STANDARD |

Move Segments:

| | |
|---|---|
| Type | Reset Extension |
| Status | DISABLE |
| Direction | NO CHANGE |
| Acquisition | INACTIVE |
| Data Points | 0 |
| End Action | CONTINUE |
| Message | |
| Type | Read Strain Gauge to Adjust Gauge Length |
| Status | DISABLE |
| Direction | NO CHANGE |
| Acquisition | INACTIVE |
| Data Points | 0 |
| End Action | CONTINUE |
| Message | Read Strain Gauge To Adjust Gauge Length |
| Type | Go to Elongation at Constant Speed |
| Status | ENABLE |
| Direction | UP |
| Acquisition | ACTIVE |
| Data Points | 500 |
| End Action | STOP |
| Message | |
| Type | Go to Elongation at Constant Speed |
| Status | DISABLE |
| Direction | NO CHANGE |
| Acquisition | INACTIVE |
| Data Points | 50 |
| End Action | CONTINUE |
| Message | Go to Elongation @ Crosshead Speed |
| Type | Go to Elongation at Constant Speed |
| Status | DISABLE |
| Direction | NO CHANGE |
| Acquisition | INACTIVE |
| Data Points | 250 |
| End Action | CONTINUE |
| Message | Go to Elongation @ Crosshead Speed |
| Type | Go to Elongation at Constant Speed |
| Status | DISABLE |
| Direction | NO CHANGE |
| Acquisition | INACTIVE |
| Data Points | 250 |
| End Action | CONTINUE |

-continued

Move Segments:

| | |
|---|---|
| Message | Go to Elongation @ Crosshead Speed |
| Type | Go Forever at Constant Speed |
| Status | DISABLE |
| Direction | UP |
| Acquisition | ACTIVE |
| Data Points | 500 |
| End Action | STOP |
| Message | Go Forever |

Sample Inputs:

| # | Label | Default | Reset Extension |
|---|---|---|---|
| 0 | JML | October 1995 | HIDDEN |
| 1 | QA Review Date: | December 1995 | HIDDEN |
| 2 | QA Version 1 | | HIDDEN |
| 3 | Sample Comment: | | OPTIONAL |
| 4 | User Input 5 | User Default 5 | HIDDEN |
| 5 | User Input 6 | User Default 6 | HIDDEN |
| 6 | User Input 7 | User Default 7 | HIDDEN |
| 7 | User Input 8 | User Default 8 | HIDDEN |
| 8 | User Input 9 | User Default 9 | HIDDEN |
| 9 | User Input 10 | User Default 10 | HIDDEN |

Sample Naming Format:

| | | | |
|---|---|---|---|
| Alias | STP | Length = | 4 |
| Alias | SAMPLE ID | Length = | 26 |
| Alias | | Length = | 0 |
| Alias | | Length = | 0 |
| Alias | | Length = | 0 |

Channel Mapping:

| # | Label | Units Class | Status | Formula | |
|---|---|---|---|---|---|
| [0] | EX-TENSION | DIMENSION | ACTIVE | P0 | (Primary Strain) |
| [1] | TIME | TIME | ACTIVE | P1 | |
| [2] | LOAD | LOAD | ACTIVE | P2 | |
| [3] | LOGICAL 3 | DIMENSION | INACTIVE | P3 | (Secondary Strain) |
| [4] | LOGICAL 4 | DIMENSION | INACTIVE | P4 | |

Report Header:
Kimberly-Clark Corporation
Peel Adhesion
Developmental Only!

Built in Reports:

Fixed Report (2)

Built-In Report #0

| | |
|---|---|
| Print Header | Y |
| Print Sample Info | Y |
| Print Individual Specimens | Y |
| Print Stats | Y |

-continued

Built in Reports:

Fixed Report (2)

| | |
|---|---|
| Print Calc Inputs | N |
| Print Test Inputs | Y |
| Print Comments | Y |

Built-In Report #1

| | |
|---|---|
| Print Header | Y |
| Print Sample Info | Y |
| Print Individual Specimens | Y |
| Print Stats | Y |
| Print Calc Inputs | N |
| Print Test Inputs | Y |
| Print Comments | Y |

Display Units:

| | |
|---|---|
| Load | Gm |
| Extension | In |
| Speed | In/Min |

-continued

Display Units:

| | |
|---|---|
| Area | Sq.In |
| Strain | % |
| Time | Min |
| Stress | PSI |

Specimen inputs:

| # | Label | Units | Default | Attribute | Panel Input | Reference |
|---|---|---|---|---|---|---|
| 0 | Thickness | In | 0.500 | HIDDEN | N | |
| 1 | Width | In | 3.000 | HIDDEN | N | Rslt 6, 15, 16, 17, 18, 24, 25 |
| 2 | Area | Sq.In | 0.125 | HIDDEN | N | Req 0 |
| 3 | Misc.Input 1 | (none) | 1.00 | HIDDEN | N | |
| 4 | Misc.Input 2 | (none) | 1.00 | HIDDEN | N | |
| 5 | Misc.Input 3 | (none) | 1.00 | HIDDEN | N | |
| 6 | Misc.Input 4 | (none) | 1.00 | HIDDEN | N | |

Calculation Inputs:

| # | Label | Units | Default | Attribute | Panel Input | Reference |
|---|---|---|---|---|---|---|
| 0 | Gage Length | In | 2.00 | OPTIONAL | Y | Req 2, 9 |
| 1 | Brk % Drop | % | 10 | HIDDEN | N | Rel 2 |
| 2 | Brk Drop Elong | In | 0.20 | HIDDEN | N | |
| 3 | Brk load | Lb | 0.20 | HIDDEN | N | Req 3 |
| 4 | Elong Point 1 | In | 0.10 | HIDDEN | N | Rslt 7, 8, 9 |
| 5 | Peel Start | In | 0.00 | OPTIONAL | Y | Rslt 10, 11, 12, 13, 14, 15, 16 |
| 6 | Peel End | In | 4.25 | OPTIONAL | Y | Rslt 10, 11, 12, 13, 14, 15, 16 |
| 7 | Elong @Mkr "S" | In | 0.00 | HIDDEN | N | |
| 8 | Elong @Mkr "P" | In | 8.00 | HIDDEN | N | |
| 9 | Sled Weight | Gm | 100 | HIDDEN | N | Rslt 31, 32 |
| 10 | Tear Criterion | % | 10 | HIDDEN | N | |
| 11 | Stress Factor | (none) | 1.333 | HIDDEN | N | Rslt 33 |
| 12 | Slack Pre-Load | Lb | 5.00 | HIDDEN | N | |
| 13 | Unity | (none) | 1.000 | HIDDEN | N | Rslt 6, 15, 16, 17, 18, 24, 25 |
| 14 | "N" peaks | (none) | 10 | HIDDEN | N | |
| 15 | "N" valleys | (none) | 10 | HIDDEN | N | |
| 16 | Peak Criteria | % | 5.0 | HIDDEN | N | |
| 17 | Valley Criteria | % | 5.0 | HIDDEN | N | |
| 18 | ChrdMod Ld1 | Lb | 5.00 | HIDDEN | N | |
| 19 | ChrdMod Ld2 | Lb | 5.00 | HIDDEN | N | |

Test Inputs:

| # | Label | Units | Default | Attribute | Panel Input | Reference |
|---|---|---|---|---|---|---|
| 0 | Crosshead Speed | In/Min | 12.00 | DISPLAY | Y | MSeg 2, 3, 4, 5, 6 |
| 1 | Load Limit HI | Gm | 12000 | OPTIONAL | N | |
| 2 | Load Limit LO | Lb | −1000 | HIDDEN | N | |
| 3 | Ext Limit HI | In | 20.00 | HIDDEN | N | |
| 4 | Ext Limit LO | In | −1.0 | HIDDEN | N | |
| 5 | Strain Limit HI | % | 300000.0 | HIDDEN | N | |
| 6 | Strain Limit LO | % | −300000.0 | HIDDEN | N | |
| 7 | Stress Limit HI | PSI | 2999999.9 | HIDDEN | N | |
| 8 | Stress Limit LO | PSI | −3000000 | HIDDEN | N | |
| 9 | # Cycles | (none) | 20.0 | HIDDEN | N | |
| 10 | Time Limit | Sec | 10000 | HIDDEN | N | |
| 11 | Brk Sensitivity | % | 110 | HIDDEN | N | |

-continued

Test Inputs:

| # | Label | Units | Default | Attribute | Panel Input | Reference |
|---|---|---|---|---|---|---|
| 12 | RETURN Point | In | 0.0 | HIDDEN | N | |
| 13 | Test End | In | 4.50 | DISPLAY | Y | MSeg 2 |
| 14 | Elong Point2 | In | 0.00 | HIDDEN | N | MSeg 3 |
| 15 | Elong Point3 | In | 2.00 | HIDDEN | N | MSeg 4 |
| 16 | Elong Point4 | In | 0.50 | HIDDEN | N | MSeg 5 |

Required Markers:

| # | Category | Code | Attribute |
|---|---|---|---|
| 1 | BREAK POINT | F | HIDDEN |
| 2 | YIELD POINT | Y | HIDDEN |
| 3 | MODULUS BEGIN | B | HIDDEN |
| 4 | MODULUS END | M | HIDDEN |

Required Calculations:

| # | Category | Procedure | Inputs |
|---|---|---|---|
| 3 | SECONDARY STRAIN | 1/ADJ_GAGE | C03 |
| 4 | BREAK | INACTIVE | |
| 5 | YIELD POINT | INACTIVE | |
| 6 | PRIMARY SLOPE | INACTIVE | |
| 7 | SLACK COMPENSATION | INACTIVE | |

Optional Markers:

| # | Category | Code | Attribute | Formula | Inputs | Reference |
|---|---|---|---|---|---|---|
| 5 | AT ELONGATION | S | MOVABLE | | C07 | |
| 6 | AT ELONGATION | E | MOVABLE | | C08 | |
| 7 | AT TEAR | T | HIDDEN | | C10 | |
| 8 | AT PIP | 1 | HIDDEN | | | |
| 9 | AT PIP | 2 | HIDDEN | | | |
| 10 | AT PIP | 3 | HIDDEN | | | |
| 11 | AT PIP | 4 | HIDDEN | | | |
| 12 | FREE | 5 | HIDDEN | @INDEX(LOAD, PEAK) | | |
| 13 | FREE | 6 | HIDDEN | @INDEX(LOAD, PEAK) | | |
| 14 | FREE | 7 | HIDDEN | @INDEX(LOAD, PEAK) | | |
| 15 | FREE | 8 | HIDDEN | @INDEX(LOAD, PEAK) | | |
| 16 | FREE | 9 | HIDDEN | @INDEX(LOAD, PEAK) | | |

Required Calculations:

| # | Category | Procedure | Inputs |
|---|---|---|---|
| 0 | AREA | CONSTANT | S02 |
| 1 | STRESS | 1/AREA | |
| 2 | PRIMARY STRAIN | 1/ADJ_GAGE | C00 C01 |
| 8 | OFFSET YIELD | INACTIVE | |
| 9 | GAGE LENGTH ADJUSTMENT | INACTIVE | C00 |

Result Calculations

| # | Label | Category | Formula | Units | Attribute |
|---|---|---|---|---|---|
| 0 | Peak Load | FIXED | PEAKLOAD | Gm | DISPLAY |
| 1 | Ave "N" Peaks | BUILT IN | AVERAGE OF "N" PEAKS MARKER-MA... | Lb | INACTIVE |
| 2 | Ave "N" MinPeaks | BUILT IN | AVERAGE OF "N" MIN PEAKS MKR-MK... | Lb | INACTIVE |
| 3 | Median Peak | BUILT IN | MEDIAN PEAKS VALUE MKR-MKR | Lb | INACTIVE |
| 4 | Ave "N" Val | BUILT IN | AVERAGE OF "N" VALLEYS MARKER-... | Lb | INACTIVE |
| 5 | Energy to Pk Ld | FIXED | @ENERGY(INDEX, START, PEAK) | In-Lb | INACTIVE |
| 6 | Linear Pk Strss | FIXED | PEAKLOAD/(S01 * C13) | Lb/In | INACTIVE |

-continued

Result Calculations

| # | Label | Category | Formula | Units | Attribute |
|---|---|---|---|---|---|
| 7 | Load @ Elong1 | FIXED | @LOAD(EXT, C04) | Lb | INACTIVE |
| 8 | Energy to Elong | FIXED | @ENERGY(EXT, 0, C04) | In-Lb | INACTIVE |
| 9 | Max Ld @ Elong1 | FIXED | @MAXLOAD(EXT, 0, C04) | Lb | INACTIVE |
| 10 | Max Ld E2-E3 | FIXED | @MAXLOAD(EXT, C05, C06) | Lb | INACTIVE |
| 11 | Min Ld E2-E3 | FIXED | @MINLOAD(EXT, C05, C06) | Lb | INACTIVE |
| 12 | Avg Ld | FIXED | @AVELOAD(EXT, C05, C06) | Gm | DISPLAY |
| 13 | Scatter E2-E3 | FIXED | @SCTRLOAD(EXT, C05, C06) | Lb | INACTIVE |
| 14 | Energy E2-E3 | FIXED | @ENERGY(EXT, C05, C06) | In-Lb | INACTIVE |
| 15 | L.Mx.Strs E2-E3 | FIXED | (@MAXLOAD(EXT, C05, C06)/C13)/S01 | Lb/In | INACTIVE |
| 16 | L.Mn.Strs E2-E3 | FIXED | (@MINLOAD(EXT, C05, C06)/C13)/S01 | Lb/In | INACTIVE |
| 17 | L.Av.Strs E2-E3 | FIXED | (@AVELOAD(EXT, C05, C06)/C13)/S01 | Lb/In | INACTIVE |
| 18 | L.Sc.Strs E2-E3 | FIXED | (@SCTRLOAD(EXT, C05, C06)/C13)/S01 | Lb/In | INACTIVE |
| 19 | Max Ld S-P | FIXED | @MAXLOAD(MARKER, 5, 6) | Lb | INACTIVE |
| 20 | Min Ld. S-P | FIXED | @MINLOAD(MARKER, 5, 6) | Lb | INACTIVE |
| 21 | Avg Ld | FIXED | @AVELOAD(MARKER, 5, 6) | Gm | INACTIVE |
| 22 | Scatter Ld S-P | FIXED | @SCTRLOAD(MARKER, 5, 6) | Lb | INACTIVE |
| 23 | Energy S-P | FIXED | @ENERGY(MARKER, 5, 6) | In-Lb | INACTIVE |
| 24 | L.Mx.Strs S-P | FREE | (@MAXLOAD(MARKER, 5, 6)/C13)/S01 | Lb/In | INACTIVE |
| 25 | L.Mn.Strs S-P | FREE | (@MINLOAD(MARKER, 5, 6)/C13)/S01 | Lb/In | INACTIVE |
| 26 | L.Av.Strs S-P | FREE | (@MINLOAD(MARKER, 5, 6)/C13)/S01 | Lb/In | INACTIVE |
| 27 | L.Sc.Strs S-P | FREE | (@AVELOAD(MARKER, 5, 6)/C13)/S01 | Lb/In | INACTIVE |
| 28 | Total Energy | FREE | (@SCTRLOAD(MARKER, 5, 6)/C13)/S01 | In-Lb | INACTIVE |
| 29 | Load @ Tear | FREE | @ENERGY(INDEX, START, END) | Lb | INACTIVE |
| 30 | Lin Ld at tear | FREE | @LOAD(MARKER, 7) | Lb/In | INACTIVE |
| 31 | Static COF | FREE | @LOAD(MARKER, 7)/C09 | (none) | INACTIVE |
| 32 | Dynamic COF | FREE | @AVELOAD(MARKER, 5, 6)/C09 | (none) | INACTIVE |
| 33 | Peak Load Cor | FREE | @STRESS(INDEX, PEAK)/C11 | PSI | INACTIVE |

Upload and Sample Reports:

| | |
|---|---|
| Free Form Sample Report | Fixed Report (1) |
| Free Form Upload Report | <None> |
| Upload Destination | COMM PORT |
| Upload Filename | DATA.TMP |

Test Page Windows:

| | |
|---|---|
| Show Load Meter | Y |
| Show Extension Meter | Y |
| Show Strain1 Meter | N |
| Show Strain2 Meter | N |
| Show Machine Status | N |
| Show Test Messages | N |
| Show Auto Extensometer | N |
| Show Description | N |
| Show Panel | Y |
| Show Machine | Y |
| Show Multi-Display | N |
| Show Handset | N |
| Show Ruler | N |
| Show Peaks | N |

Ruler Defaults:

| | |
|---|---|
| Ruler Maximum Up | 40.000000 |
| Ruler Maximum Down | −40.000000 |
| Ruler Control Mode | POSITION |
| Ruler Units | In |

-continued

Ruler Defaults:

| | |
|---|---|
| Ruler Gage Length | 1.000000 |
| Ruler Gage Length Units | In |
| Ruler Decimals Precision | 1 |

Meter Defaults:

| | |
|---|---|
| Load Meter Full Scale | 100.000000 |
| Load Meter Units | Gm |
| Load Meter Decimals | 2 |
| Load Meter Mode | DIGITAL |
| Extension Meter Full Scale | 1.000000 |
| Extension Meter Units | In |
| Extension Meter Decimals | 2 |
| Extension Meter Mode | DIGITAL |
| Strain1 Meter Full Scale | 1.000000 |
| Strain1 Meter Units | In |
| Strain1 Meter Decimals | 1 |
| Strain1 MeterMode | ANALOG |
| Strain2 Meter Full Scale | 1.000000 |
| Strain2 Meter Units | In |
| Strain2 Meter Decimals | 1 |
| Strain2 Meter Mode | ANALOG |

Peaks Defaults:

| | |
|---|---|
| Show Load Peak | Y |
| Load Units | Lb |
| Load Decimals | 1 |

-continued

| Peaks Defaults: | |
| --- | --- |
| Show Extension Peak | Y |
| Extension Units | In |
| Extension Decimals | 1 |
| Show Strain Peak | Y |
| Stain Units | % |
| Strain Decimals | 1 |
| Show Stress Peak | Y |
| Strain Units | PSI |
| Strain Decimals | 1 |
| Show Cycle Count | Y |

| Panel End Action Defaults: | |
| --- | --- |
| Load End Action | STOP |
| Extension End Action | STOP |
| Strain End Action | STOP |
| Stress End Action | STOP |

What is claimed is:

1. An absorbent garment comprising:
a front body panel comprising a terminal waist edge and a terminal crotch edge;
a rear body panel comprising a terminal waist edge and a terminal crotch edge, wherein said terminal crotch edge of said rear body panel is longitudinally spaced from and forms a gap with said terminal crotch edge of said front body panel; and
an absorbent insert comprising first and second longitudinally spaced end portions and opposite laterally spaced side edges, wherein said absorbent insert bridges said gap between said front and rear body panels with said first and second end portions overlying and connected to said front and rear body panels respectively;
wherein one of said first and second end portions of said absorbent insert is connected respectively to a corresponding one of said front and rear body panels with at least first and second adhesive regions having first and second corresponding adhesive properties respectively, wherein said first and second corresponding adhesive properties have different values, wherein said first adhesive region is positioned between said second adhesive region and said terminal waist edge of said corresponding one of said front and rear body panels and wherein said second adhesive region is positioned between said first adhesive region and said terminal crotch edge of said corresponding one of said front and rear body panels, wherein said first and second corresponding adhesive properties of said first and second adhesive regions comprise first and second adhesive basis weights respectively, wherein said second adhesive basis weight is greater than said first adhesive basis weight.

2. The absorbent garment of claim 1 wherein each of said first and second end portions of said absorbent insert are connected respectively to said corresponding ones of said front and rear body panels with at least said first and second adhesive regions having said first and second adhesive basis weights, wherein said second adhesive regions are located adjacent said terminal crotch edges of said front and rear body panels respectively, and wherein said second adhesive basis weight of said second adhesive region connecting said first end portion of said absorbent insert and said front body panel is greater than said first adhesive basis weight of said first adhesive region connecting said first end portion of said absorbent insert and said front body panel, and wherein said second adhesive basis weight of said second adhesive region connecting said second end portion of said absorbent insert and said rear body panel is greater than said first adhesive basis weight of said first adhesive region connecting said second end portion of said absorbent insert and said rear body panel.

3. The absorbent garment of claim 1 wherein said first adhesive basis weight is between about 5 gsm and about 15 gsm and wherein said second adhesive basis weight is between about 20 gsm and about 50 gsm.

4. The absorbent garment of claim 1 wherein said first adhesive region comprises an adhesive intermittently applied between said at least one of said first and second end portions of said absorbent insert and said corresponding one of said front and rear body panels.

5. The absorbent garment of claim 1 wherein said first adhesive region extends across substantially an entirety of said at least one of said first and second end portions that overlaps said corresponding ones of said front and rear body panels and that is not connected with said second adhesive region.

6. The absorbent garment of claim 1 wherein at least a portion of said second adhesive region is located adjacent said terminal crotch edge of said at least one of said front and rear body panels.

7. The absorbent garment of claim 1 wherein said second adhesive region extends between said opposite laterally spaced side edges of said absorbent insert.

8. The absorbent garment of claim 1 wherein said first and second adhesive regions further comprise third and fourth corresponding adhesive properties, wherein said third and fourth corresponding adhesive properties of said first and second adhesive regions comprise peel strengths, wherein first adhesive region has a first peel strength and wherein said first and second adhesive regions in combination have a second peel strength, wherein said second peel strength is greater than said first peel strength.

9. The absorbent garment of claim 8 wherein each of said first and second end portions of said absorbent insert are connected respectively to said corresponding ones of said front and rear body panels with at least said first and second adhesive regions, wherein said second adhesive regions are located adjacent said terminal crotch edges of said front and rear body panels respectively, and wherein said second peel strength of said first and second adhesive regions connecting said first end portion of said absorbent insert and said front body panel is greater than said first peel strength of said first adhesive region connecting said first end portion of said absorbent insert and said front body panel, and wherein said second peel strength of said first and second adhesive regions connecting said second end portion of said absorbent insert and said rear body panel is greater than said first peel strength of said first adhesive region connecting said second end portion of said absorbent insert and said rear body panel.

10. The absorbent garment of claim 8 wherein said first peel strength is measured in a longitudinal machine-direction and is a mean peak load of less than about 1500 grams, and wherein said second peel strength is measured in a longitudinal machine direction and is a mean peak load of greater than about 2000 grams.

11. The absorbent garment of claim 10 wherein said first peel strength is between about 1200 grams and about 1400 grams, and wherein said second peel strength is between about 6,500 grams and about 7,500 grams.

12. The absorbent garment of claim 8 wherein said first adhesive region extends across substantially an entirety of said at least one of said first and second end portions that overlaps said corresponding ones of said front and rear body panels and that is not connected with said second adhesive region.

13. The absorbent garment of claim 8 wherein said absorbent insert comprises an outer layer comprising a stretchable material.

14. The absorbent garment of claim 8 wherein a garment side of said absorbent insert is connected to a body side of said front and rear body panels.

15. The absorbent garment of claim 8 wherein a body side of said absorbent insert is connected to a garment side of said front and rear body panels.

16. The absorbent garment of claim 8 wherein said second adhesive region extends between said opposite laterally spaced side edges of said absorbent insert.

17. An absorbent garment comprising:
 a front body panel comprising a terminal waist edge and a terminal crotch edge;
 a rear body panel comprising a terminal waist edge and a terminal crotch edge, wherein said terminal crotch edge of said rear body panel is longitudinally spaced from and forms a gap with said terminal crotch edge of said front body panel; and
 an absorbent insert comprising first and second longitudinally spaced end portions and opposite laterally spaced side edges, wherein said absorbent insert bridges said gap between said front and rear body panels with said first and second end portions overlying and connected to said front and rear body panels respectively, wherein said absorbent insert comprises an outer layer comprising a stretchable material;
 wherein at least one of said first and second end portions of said absorbent insert is connected respectively to a corresponding one of said front and rear body panels with at least first and second adhesive regions having first and second corresponding adhesive Properties respectively, wherein said first and second corresponding adhesive properties have different values, wherein said first and second corresponding adhesive properties of said first and second adhesive regions comprise first and second adhesive basis weights respectively, wherein said second adhesive basis weight is greater than said first adhesive basis weight.

18. An absorbent garment comprising:
 a front body panel comprising a terminal waist edge and a terminal crotch edge;
 a rear body panel comprising a terminal waist edge and a terminal crotch edge, wherein said terminal crotch edge of said rear body panel is longitudinally spaced from and forms a gap with said terminal crotch edge of said front body panel; and
 an absorbent insert comprising first and second longitudinally spaced end portions and opposite laterally spaced side edges, wherein said absorbent insert bridges said gap between said front and rear body panels with said first and second end portions overlying and connected to said front and rear body panels respectively, wherein a garment side of said absorbent insert is connected to a body side of said front and rear body panels;
 wherein at least one of said first and second end portions of said absorbent insert is connected respectively to a corresponding one of said front and rear body panels with at least first and second adhesive regions having first and second corresponding adhesive properties respectively, wherein said first and second corresponding adhesive properties have different values, wherein said first and second corresponding adhesive properties of said first and second adhesive regions comprise first and second adhesive basis weights respectively, wherein said second adhesive basis weight is greater than said first adhesive basis weight.

19. An absorbent garment comprising:
 a front body panel comprising a terminal waist edge and a terminal crotch edge;
 a rear body panel comprising a terminal waist edge and a terminal crotch edge, wherein said terminal crotch edge of said rear body panel is longitudinally spaced from and forms a gap with said terminal crotch edge of said front body panel; and
 an absorbent insert comprising first and second longitudinally spaced end portions and opposite laterally spaced side edges, wherein said absorbent insert bridges said gap between said front and rear body panels with said first and second end portions overlying and connected to said front and rear body panels respectively, wherein a body side of said absorbent insert is connected to a garment side of said front and rear body panels;
 wherein at least one of said first and second end portions of said absorbent insert is connected respectively to a corresponding one of said front and rear body panels with at least first and second adhesive regions having first and second corresponding adhesive properties respectively, wherein said first and second corresponding adhesive properties have different values, wherein said first and second corresponding adhesive properties of said first and second adhesive regions comprise first and second adhesive basis weights respectively, wherein said second adhesive basis weight is greater than said first adhesive basis weight.

\* \* \* \* \*